US009380788B2

(12) United States Patent
Kritzman

(10) Patent No.: US 9,380,788 B2
(45) Date of Patent: Jul. 5, 2016

(54) PACKAGE FOR PLANT ANTIMICROBIAL TREATMENT

(71) Applicant: Nobactra Israel Ltd., Sde Warburg (IL)

(72) Inventor: Giora Kritzman, Raanana (IL)

(73) Assignee: NOBACTRA ISRAEL LTD., Sde Warburg (IL)

(*) Notice: Subject to any disclaimer, the term of this patent is extended or adjusted under 35 U.S.C. 154(b) by 0 days.

(21) Appl. No.: 14/441,829

(22) PCT Filed: Apr. 10, 2014

(86) PCT No.: PCT/IL2014/050348
§ 371 (c)(1),
(2) Date: May 8, 2015

(87) PCT Pub. No.: WO2014/170894
PCT Pub. Date: Oct. 23, 2014

(65) Prior Publication Data
US 2015/0282491 A1    Oct. 8, 2015

(30) Foreign Application Priority Data

Apr. 18, 2013    (IL) .......................................... 225825

(51) Int. Cl.
| | | |
|---|---|---|
| *A01N 63/00* | (2006.01) | |
| *A01N 65/22* | (2009.01) | |
| *A01N 65/00* | (2009.01) | |
| *A01N 65/08* | (2009.01) | |
| *B65D 75/36* | (2006.01) | |
| *B65D 81/32* | (2006.01) | |
| *A01N 25/04* | (2006.01) | |
| *A01N 25/08* | (2006.01) | |

(52) U.S. Cl.
CPC ................. *A01N 65/22* (2013.01); *A01N 25/04* (2013.01); *A01N 25/08* (2013.01); *A01N 65/00* (2013.01); *A01N 65/08* (2013.01); *B65D 75/367* (2013.01); *B65D 81/3261* (2013.01)

(58) Field of Classification Search
None
See application file for complete search history.

(56) References Cited

U.S. PATENT DOCUMENTS

| | | | |
|---|---|---|---|
| 6,495,133 | B1 | 12/2002 | Xue |
| 7,351,417 | B2 | 4/2008 | Barrow et al. |
| 7,485,451 | B2 | 2/2009 | VanderGheynst et al. |
| 8,299,162 | B2 | 10/2012 | Mateu et al. |
| 2005/0214337 | A1 | 9/2005 | McGee et al. |
| 2007/0029800 | A1 | 2/2007 | Yamashita et al. |
| 2011/0014596 | A1 | 1/2011 | Kurenov et al. |
| 2011/0028500 | A1 | 2/2011 | Su et al. |
| 2012/0083412 | A1* | 4/2012 | Trevino .................. A01N 25/26 504/117 |

FOREIGN PATENT DOCUMENTS

| | | |
|---|---|---|
| GB | 2376887 A | 12/2002 |
| GB | 2449876 A | 12/2008 |
| IN | 3603/CHE/2010 | 12/2010 |
| JP | 2010-150178 A | 7/2010 |
| WO | 2004/034791 A1 | 4/2004 |
| WO | 2004/060231 A1 | 7/2004 |
| WO | 2004/073689 A1 | 9/2004 |
| WO | 2006/057974 A1 | 6/2006 |
| WO | 2006/060213 A2 | 6/2006 |

OTHER PUBLICATIONS

Lanteigne et al. Phytophatology. 2012, 102 (10):967-973.*
Olanya et al. "Efficacy of essential oils and biopesticides on Phytophthora infestans suppression in laboratory and growth chamber studies". Biocontrol Science and Technology. vol. 16, Issue 9, 2006, pp. 901-917.*
Kleitman et al., "Characterization of a *Clavibacter michiganensis* Subsp. *michiganensis* Population in Israel", European Journal of Plant Pathology, vol. 121, 2008, pp. 463-475.
Lanteigne et al., "Production of DAPG and HCN by *Pseudomonas* sp LBUM300 Contributes to the Biological Control of Bacterial Canker of Tomato", Phytopathology, vol. 102, No. 10, 2012, pp. 967-973.
Pouvova et al., "Effectivty of Plant Essential Oils Against Clavibacter michiganensis, In Vitro", Zemdirbyste-Agriculture, vol. 95, No. 3, 2008, pp. 440-446.
Ślusarski, Czesiaw, "Attempts at Biological Control of *Clavibacter michiganensis* Subsp. *michiganensis* on Rockwool-Grown Greenhouse Tomatoes", Vegetable Crops Research Bulletin, vol. 69, 2008, pp. 125-134.
Talibi et al., "Antibacterial Activity of Moroccan Plants Extracts Against *Clavibacter michiganesis* Subsp. *michiganensis*, the Causal Agent of Tomatoes Bacterial Canker", Journal of Medicinal Plants Research, vol. 5, No. 17, Sep. 9, 2011, pp. 4332-4338.

* cited by examiner

*Primary Examiner* — Vera Afremova
(74) *Attorney, Agent, or Firm* — Morrison & Foerster, LLP

(57) ABSTRACT

The present invention provides a package (200) comprising at least one first component in the form of a well (220), the first component comprising particulate matter comprising at least one natural oil; at least one second component, in the form of a plurality of second wells (230) comprising antagonist(s) of a microbial pathogen; wherein the at least one first component and the at least one second component are contained in separate compartments of said package. Also provided by the present invention is a method for providing an anti-bacterial agent, the method comprising mixing the first component comprising particulate matter carrying at least one natural oil; and at least one second component comprising at least one antagonist of a microbial pathogen, and allowing said mixture to form into an emulsion with anti-bacterial activity. Further provided by the present invention is a method of treating or preventing a pathogen infection in a plant, the method comprises applying to said plant an amount of an emulsion comprising particulate matter, at least one natural oil and at least one antagonist of a microbial pathogen that causes said pathogen infection. Yet further, there are provided some isolated antagonistic bacteria that may be used, inter alia, in the package and methods disclosed herein.

16 Claims, 9 Drawing Sheets

PACKAGE FOR PLANT ANTIMICROBIAL TREATMENT

CROSS REFERENCE TO RELATED APPLICATIONS

This application is a U.S. national stage application of PCT/IL2014/050348, filed internationally on Apr. 10, 2014, which is incorporated herein by reference in its entirety and which claims priority to Israeli Patent Application No. 225825, filed Apr. 18, 2013.

TECHNOLOGICAL FIELD

The present disclosure is in the field of products for antimicrobial use and in particular, plant protection and biological control of plants.

PRIOR ART

References considered to be relevant as background to the presently disclosed subject matter are listed below:
US patent application publications No. US2011028500
US patent application publication No. US2011014596
Indian Patent Application No. IN03603CH2010
U.S. Pat. No. 7,485,451
Ait Ben Aoumar A. et al. J. Med. Plants Res. 6(17):4332-4338, 2011
Pouvova D. et al. Zemdirbyste-Agrucyktyre 95(3):440-446, 2008
Lanteigne C, et al. Phytopathology.102(10):967-73, 2012
Slusarski C. Vegetable Crop Research Bulletin 69:125-134 2008

Acknowledgement of the above references herein is not to be inferred as meaning that these are in any way relevant to the patentability of the presently disclosed subject matter.

BACKGROUND

Agricultural crops are susceptible to a large variety of microbial pathogens, which results in annual losses and economical damages. Methods developed to protect crops from plant diseases include plant breeding for resistance, cultural practices, application of chemical agents, and biological control.

As the use of chemical pesticides resulted in severe environmental pollution, and many pathogens are developing resistance to existing chemicals, many pesticides are now banned for use, and organic farming is not allowed to rely on such substances at all. Thus, a major goal, therefore, is to develop new, environmentally-friendly tools to control pathogens, namely, biological control techniques.

U.S. Pat. No. 6,495,133 describes a strain of *Glicladium roseum* exhibiting antagonistic effects against plant pathogens. The biocontrol agent is used in treatment o seeds, soil or plants to protect against fungal pathogens of various plants, including tomato.

US patent applications publications Nos. US2011028500 and US2011014596 describe a plant pathogen inhibitor combination comprising a plant extract containing one or more anthraquinone; an anti-phytopathogenic agent which may include natural oil or oil product having fungicidal activity.

Indian Patent Application No. IN03603CH2010 describes an invert-emulsion formulation of fungal organisms as biological control. The formulation is in the form of an invert emulsion formulation. The process described includes production of fungal spores either by solid state or liquid fermentation; preparation of conidial suspension or cell suspension; preparation of aqueous phase by mixing the conidial suspension, water, emulsifier and glycerol; preparation of oil phase by adding vegetable fat mixture to a warm vegetable oil mixture; mixing of aqueous phase with oil phase to get water in oil or invert-emulsion formulation using homogenizers The product can be used for seed treatment, soil application and foliar spray.

U.S. Pat. No. 7,485,451 also describes an invert emulsions (water in oil emulsions) comprising cellular material selected from living and/or dormant prokaryotic and/or eukaryotic cells and tissues, the cellular material being compatible with water-in-oil emulsions. Examples of cellular material included fungi, watermolds, algae, yeasts, bacteria, plant, inset and animal cells. The inverted emulsion also comprises an oil, such as vegetable oil and/or fish oil as well as an oil soluble non-ionic surfactant, and water. Optionally, the composition contains a thickener, such as fumed silica or bentonite.

Essential oils having an antagonistic effect have also been investigated. For example, the antibacterial activity of Moroccan plants extracts against *Clavibacter michiganensis* subsp. *Michiganensis* (CBM), the cause of tomato bacterial canker, was described [AA Ben Aoumar A. et al. J. Med. Plants Res. 6(17):4332-4338, 2011]. In addition, the effectivity against CBM of plant essential oils from 34 aromatic plants was examined [Pouvova D. et al. Zemdirbyste-Agrucyktyre 95(3):440-446, 2008].

Recently, the simultaneous production of DAPG and HCN by *Pseudomonas* sp. LBUM300 was found to be beneficial for the biological control of tomato bacterial canker caused by *Clavibacter michiganensis* subsp. michiganensis [Lanteigne C, et al. Phytopathology. 102(10):967-73, 2012].

In addition, attempts at biological control of CBM Rockwool-grown greenhouse tomatoes was described. Specifically, artificial inoculation of two and three years old rockwool slabs with CBM bacteria dead plants reduces death rate of the plants [Slusarski C. Vegetable Crop Research Bulletin 69:125-134 2008].

GENERAL DESCRIPTION

Biological control of plant diseases generally is defined as suppression of pathogens by application of one or more organisms that exhibit antagonistic activity towards the pathogens. The organisms that act as antagonists are regarded as biological control agents (BCAs) and the mechanisms of the antagonistic effects are based on a variety of biological properties of BCAs. These comprise production of antibiotic compounds, expression of enzymes that catalyze the decomposition of cell components of pathogens, competition for space and nutrients, the ability to parasitize pathogens, and the induction of plant defense.

The present disclosure is aimed at providing a ready for use package for bio-control of crops against microbial infection as well as for preventing such infection from developing. As will be evident from the following description, there are provided packages such that the bio-control components are isolated from each other during long term storage and are easily mixed, at the pre-determined concentrations, upon need, without any risk of environmental contamination by the package's components. It has been found that the package configuration ensures chemical stability of the components, i.e. without any damage after long term storage.

Accordingly, and in accordance with a first of its aspect, the present disclosure provides a package comprising:

at least one first component comprising particulate matter comprising at least one natural oil;

at least one second component comprising at least one antagonist of a microbial pathogen;

wherein the at least one first component and the at least one second component are contained in separate compartments of said package.

In some embodiments, the compartments are defined as wells within a carrier element forming part of the package.

According to some embodiments, the package comprises:
(i) one or more first wells (compartment) holding a first component comprising particulate matter comprising at least one natural oil;
(ii) one or more second wells (compartment) holding a second component comprising at least one antagonist of a microbial pathogen;
the one or more first wells and the one or more second wells each having a top opening and a recess extending downwardly from said top opening, the wells being held together in an essentially planar matrix; and
(iii) a first film sealing the openings of the one or more first wells; and
(iv) a second film sealing the openings of the one or more second wells.

In accordance with a second of its aspects, there is provided a method for providing an anti-bacterial agent, the method comprises mixing one or more first components comprising particulate matter, the particulate matter carrying at least one natural oil with one or more second components comprising at least one antagonist of a microbial pathogen, and allowing the mixture (cocktail) thus obtained to form into an emulsion. The thus formed emulsion poses anti-bacterial activity. The emulsion prepared by the components disclosed herein is stable emulsion, i.e. where no phase separation is apparent for at least several hours, for 1, 2, 3, 4, 5, 6, 7, 8, 9, 10 and even up to 24 hours.

In some embodiments, the method makes use of the packages disclosed herein. In some embodiments, the use of the package provides a composition or an emulsion comprising particulate matter, a surfactant, at least one natural oil, and at least one bacterial antagonist of a plant pathogen. In some embodiments, the antagonist is of a time that is capable of growing on sesame oil as a sole carbon source.

In accordance with yet a third of its aspects, the present disclosure provides a method of treating or preventing a pathogen infection in a plant, the method comprises applying onto said plant an amount of an emulsion comprising particulate matter, at least one natural oil and at least one antagonist of the pathogen that causes the infection.

In accordance with a fourth of its aspects, the present disclosure provides isolated antagonistic bacteria having a representative sample deposited at the CBS-KNAW institute and bearing the accession No. selected from the group consisting of CBS133252, CBS133254, CBS133255, CBS133256, CBS133257, CBS133258, CBS133259, CBS134566, CBS134567 and CBS134568. In some embodiments, these antagonistic bacteria are for use in protecting or treating plants against a pathogen induced infection.

BRIEF DESCRIPTION OF THE DRAWINGS

In order to better understand the subject matter that is disclosed herein and to exemplify how it may be carried out in practice, embodiments will now be described, by way of non-limiting example only, with reference to the accompanying drawings, in which.

DETAILED DESCRIPTION OF EMBODIMENTS

Figure 1A:
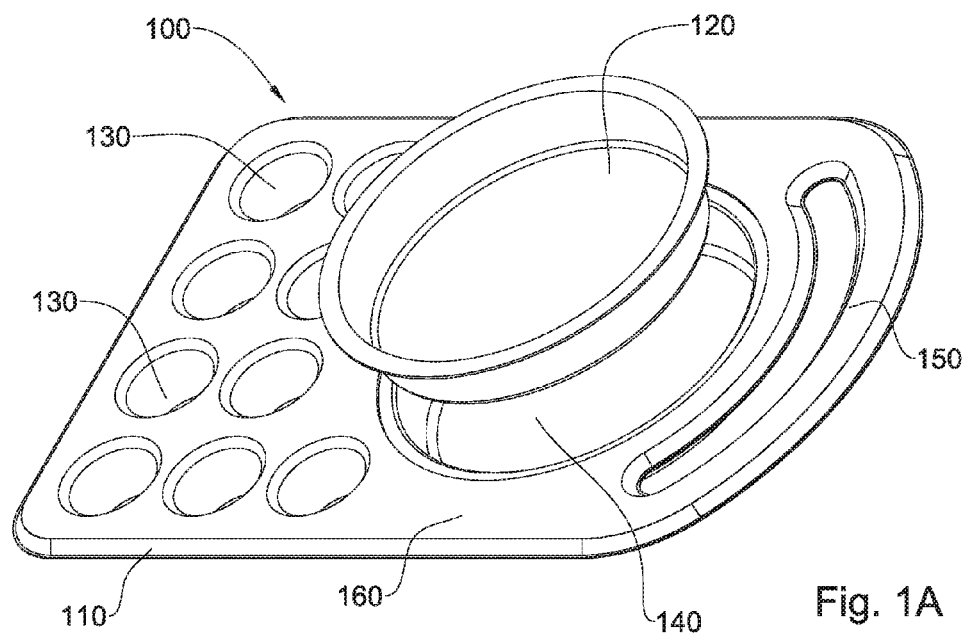
FIGS. 1A-1D show a carrier element forming part of a package according to an embodiment of the invention, from different views, with FIG. 1A providing an isometric view, FIG. 1B providing a top view and FIGS. 1C and 1D providing views from side X and side Y of FIG. 1B.

The present invention is aimed at providing a package that is suitable for long term storage and upon need, provides a safe and easy method for preparing anti-microbial compositions for various applications, such as for crop protection. To this end, a package has been developed, having two (or more) wells or set of wells, each well or set of wells carrying a different component. The package is configured such that the two (or more) wells are separately and differently sealed, due, inter alia, to different physical and chemical characteristics of the matter in the compartments, as will be further discussed hereinafter.

Generally, the package comprises:
at least one first component comprising particulate matter comprising at least one natural oil;
at least one second component comprising an antagonist of a microbial pathogen;
wherein the at least one first component and the at least one second component are contained in separate compartments of said package. In other words, as long as the kit is sealed, the two components are not mixed or are not in contact with each other.

Upon mixing of the first and second components (i.e. taking out the two components from their separate compartments), a stable emulsion is obtained, suitable for application onto the crop to be treated or protected. The emulsion is applied in a form of fine droplets.

In the context of the present disclosure, the term "particulate matter" is used to denote a substance in the form of plurality of particle. The particles may be in any particulate form, including, without limited thereto, from finely rounded beads to amorphous structures. The particulate matter includes any form of a powder.

In some embodiments, the particulate matter comprise silica dioxide ($SiO_2$, in short referred to herein as silica). The silica may be naturally occurring silica particles such as bentonite clay beads, as well as synthetic silica beads.

In some embodiments, the particulate matter comprises synthetic silica particles. There are a variety of synthetic silica particles that may be used in the context of the present disclosure. For example, the particulate matter may comprise precipitated synthetic amorphous silica beads, such as the commercially available products Tixosil and Aerosil 200.

In some other embodiments, the particulate matter comprises synthetic or nature derived beads with the capacity to absorb the natural oils. Such beads may include, without being limited thereto Latex beads; calcium carbonate sorbent particle; cellulose beads; polystyrene adsorbents beads e.g. Amberlite® XAD®-2 which is a hydrophobic crosslinked polystyrene copolymer absorbent resin; charcoal; Sepharose™ beads; emulsan-alginate beads; chitosan beads; sodium alginate; styrene-maleic acid copolymer beads and styrene-divinylbenzene beads; cellulose paper beads.

To allow good distribution of the final emulsion and in accordance with some embodiments the particulate matter (particles) has a size distribution in the range of 10-25 μm.

The particulate matter may also be characterized, without being limited thereto, by one or more of a surface area, in some embodiments, in the range of 400-500 $m^2$ $N_2$/g and oil capacity in the range of 300-350 DBP/100 gram particulate.

The first component comprises the particulate matter that holds one or a combination of natural oils. In the context of the present disclosure it is to be understood that "natural oil" encompasses any organic oil obtained from nature.

The natural oil is preferably oil derived from a plant. In some embodiments, the natural oils are known as essential oils. The essential oils are preferably those known to exhibit antimicrobial (e.g. antibacterial, antifungal, antinematodal) properties.

When referring to anti-microbial properties it is to be understood as being effective against any microbial pathogen, as further discussed below.

Without being limited thereto, essential oils to be used in accordance with the present disclosure, may be those derived from the plants *Origanum vulgare* and *Origanum* spp., (e.g. Oregano), *Mentha* spp. (mint), *Thymus* spp. (Thyme), *Myrtus* spp., *Ocimun* spp. (e.g. *Ocimun basilicum*, also klnown as Basil), *Lavandula* spp. (e.g. Lavender), *Micromeria* spp., *Coriandum* spp. (e.g. Coriander/Parsley), *Aloysia* spp., *Melissa* spp., *Salvia* spp., *Petoselinum* spp., *Rosmarinus* spp. (e.g. Rosemary), *Prunella* spp., *Cuminum* spp (e.g. Cumin).

In some other embodiments, the natural oils are plant derived oils that is used as carbon source, e.g. as food/nutrient for the antagonistic microorganisms. These are referred to herein the term "carbon-base oil" or "carbon-rich nutrient oil". In some embodiments, the carbon-base oils are vegetable oils. Without being limited thereto, the carbon-base oil is selected from the group consisting of Sesame oil, Olive oil, Peanut oil, Cottonseed oil, Soybean oil, Palm oil, sunflower oil, safflower oil, canola oil, castor oil, coconut oil, groundnut oil.

In some embodiments, the term "natural oil", when used in plurality, encompasses a combination of at least one essential oil and at least one carbon-base oil, both being of natural source.

In some embodiments, the natural oil comprises at least Oregano oil in combination with at least one carbon-base oil. The Oregano oil is combined, at times, with at least Sesame oil.

It has been unexpectedly found that the antagonistic bacteria may be distinguished from other bacteria with no exhibited antagonistic activity towards at least CBM by their capability to grow on carbon base oil, such as sesame oil. In one embodiment, the carbon base oil on which all antagonistic bacteria grow (while non-antagonistic bacteria tested do not) is sesame oil.

The amount of the natural oil within the first component (e.g. held by the particulate matter) may vary, depending on the type(s) of the natural oil used, the amount at loading, the type of particulate matter, the conditions of loading the natural oil onto the particulate matter, the surfactants or solvents used for loading etc.

When referring to loading of the oil onto the particulate matter, it is to be understood as meaning any form of association between the oil and the particulate matter (e.g. silica particles). Without being limited thereto, the oil is held by the particulate matter by absorption onto and/or into the particles. The association between the particles and the oil is reversible, namely, under suitable conditions, such as when brought into contact with water, the oil is easily released from the particles to form an emulsion.

In some embodiments, the particulate matter holds between 20% to 50% w/w natural oil out of the total weight of the particulate matter (after loading). This is determined by conventional techniques such as HPLC or GC chromatography, as also exemplified below. In some other embodiments, the particulate matter holds about 30% w/w natural oil ("about" encompasses a range of between 25-35%, at times between 28% to 32% or around 30%).

In some embodiments, the natural oil comprises either only the essential oil(s) or a combination of at least one essential oil and at least one carbon-base oil. As such, when referring to natural oils it is to be understood as encompassing essential oil(s) as well as carbon-base oil(s). The ratio between the at least one essential oil and at least one carbon-base oil is in the range of 60:40 and 100:0, at times the range is about 80:20.

When a combination of oils is used it is to be understood that they may be absorbed onto the particulate matter together, i.e. the same particulate matter holds more than one type of oil. In some embodiments, for ease of handling, each oil type is held separately on particulate matter such that different types of particulate matter are formed, each being characterized by the type of oil it is holding.

Thus, when referring to particular matter providing Oregano and Sesame at a ratio of 80:20 it is to be understood as a mixture of two populations of particulate matter, 80% carrying Oregano oil and 20% of a type carrying Sesame oil or a single population of particles, each particle being absorbed with the two oils at the defined or desired ratio (i.e. the oils are a priori mixed and then brought into contact with the absorbing carrier/particle). Irrespective of the oil type, the particulate matter between 20% to 50% w/w of its total weight it provided by the oil loaded thereon.

The particulate matter may also comprise at least one surfactant. As appreciated, a surfactant is a compound that lowers the surface tension of a liquid and as such, the interfacial tension between two liquids to allow the formation of, e.g. an emulsion. The surfactant may be of any kind known in the art as safe for use (e.g. non-toxic to plants or animals), including ionic surfactants, anionic surfactants, cationic surfactants as well as zwitterionic (or non-ionic) surfactants.

In some embodiments, the surfactant is of a type acceptable in organic agriculture. A non-limiting list of possible surfactants to be used in accordance with the present disclosure includes Polyethylene glycol sorbitan trioleates (Tween, e.g. Tween 85, Tween 65), sorbitan fatty acid esters (e.g. Span 40).

In some other embodiments, the surfactant comprises a salt of a fatty acid. The salt may comprise an alkaline such as potassium, calcium, sodium salts, as well as an ammonium salt.

In some embodiments, the salt of a fatty acid comprises potassium salts of fatty acids (also known as soap salts), which are at times used as insecticides, herbicides, fungicides, and/or algaecides. In some embodiments, potassium salts of fatty acids may be obtained by adding potassium hydroxide to natural fatty acids such as those found in animal fats and in plant oils. Fatty acids may be extracted from olives, cotton seeds, soya beans, peanuts, sun flowers, coconuts Palm, Rapeseed, Sesame oil, Amaranth, Corn, Jatropha.

The fatty acid forming the surfactant may also be a synthetic fatty acid as well as a semi-synthetic (e.g. a natural fatty acid that underwent a modification).

In accordance with some embodiments, the at least one surfactant is one being recognized or is labeled as having an insecticide and/or fungicide activity. Without being limited thereto, pesticidal and/or fungicidal surfactants may include, the commercial products Zohar PT-50 and Zohar LQ-215, both produced by Zohar Dalia, Israel.

In one particular embodiment, the surfactant is selected from Zohar PT-50 and Zohar LQ-215.

The compositions of these surfactants are available from Zohar Dalia. For instance, Zohar PT-50 is known to have the following composition:

Vegetable oils

| | | | Polyunsaturated fatty acids | | | | |
|---|---|---|---|---|---|---|---|
| Type | Saturated fatty acids | Mono-unsaturated fatty acids | Total poly | linolenic acid (ω-3) | Linoleic acid (ω-6) | Oleic acid (ω-9) | Smoke point |
| Not hydrogenated | | | | | | | |
| Canola (rapeseed) | 7.365 | 63.276 | 28.14 | 9-11 | 19-21 | — | 204° C. |
| Coconut | 91.00 | 6.000 | 3.000 | — | 2 | 6 | 177° C. |
| Corn | 12.948 | 27.576 | 54.67 | 1 | 58 | 28 | 232° C. |
| Cottonseed | 25.900 | 17.800 | 51.90 | 1 | 54 | 19 | 216° C. |
| Flaxseed/Linseed (European) | 6-9 | 10-22 | 68-89 | 56-71 | 12-18 | 10-22 | 107° C. |
| Olive | 14.00 | 72.00 | 14.00 | <1.5 | 9-20 | — | 193° C. |
| Palm | 49.300 | 37.000 | 9.300 | — | 10 | 40 | 235° C. |
| Peanut | 16.900 | 46.200 | 32.00 | — | 32 | 48 | 225° C. |
| Safflower (>70% linoleic) | 8.00 | 15.00 | 75.00 | — | — | — | 210° C. |
| Safflower (high oleic) | 7.541 | 75.221 | 12.82 | — | — | — | 210° C. |
| Soybean | 15.650 | 22.783 | 57.74 | 7 | 50 | 24 | 238° C. |
| Sunflower (<60% linoleic) | 10.100 | 45.400 | 40.10 | 0.200 | 39.800 | 45.300 | 227° C. |
| Sunflower (>70% oleic) | 9.859 | 83.689 | 3.798 | — | — | — | 227° C. |
| Fully hydrogenated | | | | | | | |
| Cottonseed (hydrog.) | 93.600 | 1.529 | .587 | | .287 | | |
| Palm (hydrogenated) | 47.500 | 40.600 | 7.50 | | | | |
| Soybean (hydrogen.) | 21.100 | 73.700 | .400 | .096 | | | |

Values as percent (%) by weight of total fat.

The results provided herein show that a salt of a fatty acid as disclosed herein had some advantage in terms of stability and/or emulsification properties of the powder, and anti-microbial activity, over other known surfactants, such as the commercially known Tween 20 or Tween 80.

The amount of the surfactant in the first component may vary. However, in some embodiments, the particulate matter comprises between 5% to 10% w/w of the surfactant or combination of surfactants.

The first component comprising the particulate matter is in an essentially dry form. When referring to "essential dry" it is to be understood that the first component may contain low amounts of water, in some embodiments not more than 10% (w/w). In some other or additional embodiments, the water content in the first component is within the range of 1% to 7% (w/w). In yet some other embodiments, the "essential dry" is to be understood as encompassing no water being detected by conventional methods (i.e. no detectable amount of water).

The first component may also contain some trace amounts of an organic solvent. As will be further discussed below, a solvent may be required for the preparation of the particulate matter and some residual amounts may remain, as long as the solvent is not toxic. In some embodiments, the first component is either solvent free (i.e. contains no detectable amounts of an organic solvent) or comprises trace amount, i.e. not more than 5%, 4%, 3% or even 2% w/w organic solvent. The solvent is typically an organic volatile polar solvent, such as, without being limited thereto, a solvent selected from the group consisting of acetone, isopropyl alcohol, acetonitrile, ethanol and methanol.

In some embodiments, trace amounts of alcohol are detected in the first component.

The particulate matter of the first component is unique in its capability of forming a stable emulsion, once the particulate matter is brought into contact with water. This is achieved, inter alia, due to the presence of a surfactant in the first component. The surfactant is added to the particles with the oil, before bringing the components into dryness.

In the context of the present disclosure, when referring to a stable emulsion it is to be understood as referring to dispersion of oil (the dispersed phase) in water (the dispersion medium) for a period of at least 1 hour, at times, at least 2, 3, 4, 5, 10 or even 24 hours following the formation of the emulsion. In other words, the stability is determined by the lack of separation into an oil phase and a water phase. The lack of separation may be determined by any means known in the art, including visible inspection.

Without being bound by theory, it is the inventor's position that the incorporation of a surfactant in the particulate matter contributes to the stability of the emulsion formed. This is also evident from the non-limiting examples provided hereinbelow, where the use of potassium salts of fatty acids showed an advantage in terms of stability and safety over other types of commercially available surfactants.

To form the emulsion, the particulate matter is mixed water. The amount of water depends on the amount of particulate matter. In some embodiments, for each gram of particulate matter (30% of which is oil), water is added to provide a one liter emulsion. As such, in a 1 liter emulsion, 0.1 gr particulate matter provides an oil concentration of 0.03% v/v). In some embodiments, the percentage of oil in the final emulsion is in the range of 0.03% and 2% v/v.

In some embodiments, the mixing of the particulate matter with water provides an emulsion with a droplet size in the range of between 1 to 20 μm and in some embodiments in the range between 3 to 10 μm.

In some embodiments, the emulsion is an anti-microbial emulsion.

The package contains a second component comprising at least one antagonist of a microbial pathogen.

In some embodiments, the at least one antagonist of a microbial pathogen held in a gel or gel-like carrier. Various materials may be used in order to form the gel form for carrying the antagonists.

For example, the gel may be formed from a polysaccharide or combination of polysaccharides with other substances.

According to some embodiments, the gel is selected from the group consisting of agar gel (agar-agar) Guar gum, gelatin, xanthan gum, methyl cellulose gel (cellulose gum), pectin base gel, gelatin gel, and others, as known in the art.

In some embodiments, the second component comprises agar-agar thereby forming a gel holding the microbial antagonists.

In the context of the present disclosure, when referring to antagonists of a microbial pathogen or a pathogen antagonist, it is to be understood as a biological entity that inhibits the plant pathogen (a plant pathogen may also be referred to as a phytopathogen). Inhibiting, in the context of the present disclosure is to be understood as reducing growth of the pathogen by at least 50%, at least 70%, at least 90% or even by essentially eliminating the pathogen. The plant pathogen, in the context of the present invention may be any prokaryotic or eukaryotic organism, including, without being limited thereto bacteria, a fungi, protozoa, nematodes, or any other disease causing parasite. As such, the microbial activity of the at least one antagonist, may any one of antibacterial, antifungal, antiprotoxoal, antinematodal etc.

In some embodiments, the second component comprises at least one antagonists. In some other embodiments, the second component comprises a cocktail of antagonists. The cocktail is to be understood as a combination of two or more, at times, 3, 4, 5, 6, 7, 8, 9, 10, 11, 12, 13, 14 or 15, antagonists combined together in the same or different concentrations.

In some embodiments, the at least one antagonist is of a type capable of growing on sesame oil as a sole carbon source, as shown in Table 3 hereinbelow. Such antagonists may be easily identified by conducting a conventional cultivation assay using sesame as the sole carbon source and identifying those cultivars that survived the experimental growing period.

In some embodiments, the antagonist may be referred to as a bacteriostate, i.e., that slows down growth of organisms, and in some other embodiments, the antagonist may be referred to as a bactriocide, namely, that kills the organism.

In some embodiments, the at least one antagonist of a microbial pathogen is a soil born antagonist. In this context it is to be understood that the at least one antagonist may be obtained and isolated from the roots, soil and/or rhizophere of a plant that was shown to be tolerant (e.g. partially resistant) or resistant to the microbial pathogen.

In some other embodiments, the at least one antagonist of a microbial pathogen is a plant derived antagonist, e.g. isolated from a plant part, such as the leaves, the stem, the flower, the vascular system.

The at least one antagonist of a microbial pathogen may also be present and thus derived from the soil (i.e. soil born) and from a plant part (e.g. the vascular system).

In accordance with some embodiments, the antagonists are of a pathogen causing infection in tomato plants.

In yet some embodiments, the antagonists are of the pathogen for which treatment is desired.

The second component may include one or more antagonists. In some embodiments, the second component includes a combination of several antagonists in the same gel. However, in some other embodiments, when combinations of antagonists are to be used, they are each carried by a separate gel and mixed only prior to use. In other words, the second component is a combination of several "second components", where each antagonist is maintained separately and depending on the type of pathogen to be treated, are combined prior to exposure of the plant.

When a combination of antagonists is used, the antagonists may be provided/applied to the plant in the same amounts (CFU/ml) or in different amounts.

In accordance with some embodiments, the amount of an antagonist in the second component (either as a single antagonist or as a cocktail of antagonists) may be in the range between 500 to 5,000 CFU/ml/. The ratio between the antagonists, when used as a cocktail may vary, depending on the type of pathogen to be treated and may be a priori determined by conventional laboratory methods, e.g. best bacteriostatic/bactriocidal effect in a cultivation dish.

The type of antagonist will depend on the type of pathogen to be treated by the package.

In some additional embodiments, the pathogen is *Clavibacter michiganensis* subsp. *Michiganensis* (CBM). In this embodiment, some antagonists that have been isolated from tomato plants that exhibited tolerance to CBM are selected from the non-limiting group consisting of *Pseudomonas* species (Accession No. CBS133252), *Pseudomonas alcaliphila* (Accession No. CBS133254), *Bacillus subtilis* (Accession No. CBS133255), *Pseudomonas cedrina* (Accession No. CBS133256), *Pseudomonas* species (Accession No. CBS 133257), *Pseudomonas* species (Accession No.CBS133258), *Pseudomonas spanius* (Accession No. CBS133259).

Other antagonists are known in the art such as those provided in Table 4 of the Report by the International Organization for Biological and Integrated Control of Noxious Animals and Plants [Edited by Philippe C. Nicot 2011], the content of which is incorporated herein by reference.

In some other embodiments, antagonists of other plants may form part of the second component of the package disclosed herein. These may include other agricultural crops, such as, without being limited thereto, those derived from the Solanaceae family, e.g. tomato, pepper, eggplant, potato; from the Cucurbitaceae family, e.g. squash, melon, gourd, cucumber, pumpkin, luff and watermelons, but also any other seed bearing plants including horticultural plants, trees etc. The package typically comprises instructions for use of the first component and the second component to form an emulsion which is to be applied onto a plant. The instructions comprise, at least mixing the first component with the second component, optionally with the addition of an amount of water, to form an emulsion. In some embodiments, the concentration of the at least one antagonist in the emulsion is at minimum 1,000 CFU/ml, or in the range of 500 CFU/ml to 5,000 CFU/ml.

In addition, antagonists may be found in various literatures, such as, without being limited thereto, the following, which are incorporated herein by reference:

| The Pathogen | The infected plant | The Antagonists | Source of information |
|---|---|---|---|
| Ralstonia Solanacearum | Tomato, Pepper | Bacillus megaterium, Enterobacter cloacae, Pichia guillermondii and Candida ethanolica | Journal of Plant Pathology 92(2): 395-406 (2010) |
| E. carotovora subsp. carotovora P-138 | | E-65 as a Bacillus sp. and E-45 as a Lactobacillus sp. | The Scientific World Journal (2012), Article ID 723293. |
| Leptosphaeria maculans | canola | Pseudomonas chlororaphis and P. aurantiaca | Biocontrol Science and Technology 16(5/6): 567582 (2006) |
| Ralstonia solanacearum (Pseudomonas solanacearum) | Fungi in peanut | Pseudomonas fluorescens RH4003 and Bacillus subtilis AB89 | J. ISSAAS Vol. 18(1): 185-192 (2012) |
| Ralstonia solanacearum | Wilt disease of potato | Pseudomonas solanacearum isolates: B82; w163; wp95 and P. fluorescens | http://www.apsnet.org/publications/PlantDisease/BackIssues/Documents/1983Articles/PlantDisease67n05_499.pdf |
| Rhizoctonia solani | potato | commercial products of Bacillus subtilis (Kodiak) Actinomycetes | Crop Protection 24(11): 939-950, (2005) Phytoprotection 82: 85-102 (2001) |
| Xanthomonas oryzae pv. oryzae | Bacterial Leaf Blight Disease in Rice | Streptomyces spp | American Journal of Agricultural and Biological Sciences 7(2): 217-223 (2012) |
| Xanthomonas oryzae pv. oryzae | | Isolates from soil and water | Rice Indstry, culture, and environment 549-553 |
| Streptomyces spp | Potato scab | | Phytopathology 85: 261-268 (1995); Can J Microbiol. 47(4): 332-40 (2001) |
| Sclerotinia sclerotiorum, Streptomyces sp. and Phytophthora capsici | Soybeans Potato scab Vegetable crops | Bacillus amyloliquefaciens (BAC03) | MSU AgBioResearch 2011 Annual Report, (2012) URL: http://research.msu.edu/stories/getting-root-soil-borne-diseases |
| Rhizoctonia solani and Fusarium sambucinum, | Black Scurf Dry rot of Potato | | Egypt. J. Phytopathol., 36(1-2): 45-56 (2008) |
| Rhizoctonia solani | Lettuce | Endophytic strains, Serratia plymuthica 3Re4-18 and Pseudomonas trivialis 3Re2-7, rhizobacterium Pseudomonas fluorescens L13-6-12 | FEMS Microbiol Ecol 64: 106-116 (2008) |
| Rhizoctonia solani | Potato | Pseudomonas fluorescens | Acta biol. Colomb. 12(1) pages XXX (2007) |
| Xanthomonas campestris pv. vesicatoria | Tomato | Rahnella aquatilis | Microbiological Research, 160(4): 343-352 (2005) |
| Erwinia amylovora (Fire Blight) | | Pseudomonas fluorescens A506, Pantoea agglomerans C9-1, and Pantoea | Plant Disease 93(4): 386 URL: http://apsjournals.apsnet.org/doi/pdf/10.1094/PDIS-93-4-0386 |

-continued

| The Pathogen | The infected plant | The Antagonists | Source of information |
|---|---|---|---|
| Erwinia amylovora (Fire Blight) | | Erwinia herbicola | ISHS Acta Horticulturae 117: II Symposium on Fireblight URL: http://www.actahort.org/books/117/117_21.htm |
| Clavibacter michiganensis subsp. michiganensis | | Bacillus subtilis; Rhodosporidium diobovatum | BioControl 49: 305-313, 2004 |

As noted above, in some embodiments, the antagonist is of a type that is capable of growing on sesame oil as a sole carbon source.

At times, for preparing the emulsion, water may be added. When water is added, the amount of water will depend on the amount of the first component. In some embodiments, for each gram of first component (e.g. 30% of which are oil), water is added to provide one liter emulsion. As such, in 1 liter emulsion, 0.1 gr particulate matter provides an oil concentration of 0.03% v/v.

In some embodiments, the percentage of oil in the final emulsion is in the range of 0.03% and 2% v/v.

According to the above, a final formulation may be provided by a package containing 20 grams of a powder of the first component (30% of which is the oil), and 120 ml of an antagonist gel of the second component and the instructions may include mixing the first component and the second component with water to form 20 liter emulsion containing 0.3%v/v of oil.

Similarly, a package may contain 50 grams or 100 grams of a powder of the first component, and 120 ml of an antagonist gel of the second component and the instructions may include mixing the first component and the second component with water to form a 50 or 100 liter emulsion.

In some embodiments, the second component is provided in the package in separate units, each unit carrying a different antagonist in gel. For example, a package containing in total 120 ml gel, the gel may constitute several gel units, each gel unit carrying the same or different antagonist, e.g. 8 gels of 15 ml gel each. This allows selecting the types of antagonists to be used and changing the combinations in the cocktail as needed, so as to provide a better biocontrol of the pathogen.

The package of the disclosure is suitable for the providence of a novel emulsion. In this respect, the present disclosure also provides an emulsion comprising particulate matter, a surfactant, at least one natural oil and at least one bacterial antagonist, all as defined herein as components of the package, wherein the at least one antagonist is of a type that will grow on sesame oil as a sole carbon source.

The package disclosed herein is particularly suitable for use in preventing or treating pathogenic infection in a plant. Treatment may include inhibition of pathogen growth (bacteriostatic effect) as well as total elimination of the pathogen infection (bacteriocidal effect).

In some embodiments, the treatment or prevention is of an infection caused by *Clavibacter michiganensis* subsp. *Michiganensis* (CBM).

In some embodiments, the treatment or prevention is of an infection caused by xanthomonas vesicatoria. In some other embodiments, the treatment or prevention is of an infection caused by *Streptomyces scabies*.

In some embodiments, the treatment or prevention is of an infection in a plant belonging to the Solanaceae family, e.g. tomato, pepper, eggplant, potato. In one embodiment, the plant is a tomato plant.

In some embodiments, the package in accordance with the present disclosure, comprises

- a carrier element comprising an essentially planar matrix holding together one or more first compartments/wells for carrying at least one first component comprising particulate matter including at least one natural oil; and one or more second wells/compartments for carrying at least one second component comprising at least one antagonist of a microbial pathogen; the one or more first wells and the one or more second wells each being defined by a top opening and a recess extending downwardly from the top opening;
- a first film sealing the openings of the one or more first wells; and
- a second film sealing the openings of the one or more second wells.

As appreciated, each well is a separate entity and mixing of content of one well with the other is possible only after opening the sealing films.

A non-limiting example of a carrier element is illustrated in FIGS. 1A-1D providing an isometric view (FIG. 1A) and top and side views (FIGS. 1B to 1D) of element 100 including a planar matrix 110 including a single first well 120 and a plurality of, spaced apart, second wells 130. In this non-limiting example, first well 120 is reversibly mountable in a depression 140 provided in planar matrix 110. In some other embodiments, a mountable well, such as well 120, may be fitted within an opening (hole) in the planar matrix 110 (not illustrated). Alternatively, the first well may be formed as an integral part of planar matrix 110 (not illustrated).

The plurality of second wells 130 are formed, in this particular embodiment, as an integral part of planar matrix 110. In an alternative embodiment, any of second well(s) 130 may be of a kind that can be reversibly mountable in a depression 140, as illustrated for first well 120 or in an opening provided in planar matrix (not shown). In accordance with this embodiment, first well 120 is in fact a type of a cup that can be removed from the depression (in the form of a holding well) the planar matrix prior to use.

Carrier element 100 also includes a gripping unit 150, in the form of a handle. The gripping unit may have other forms and shapes, so as to facilitated stable and firm holding of the carrier element when the sealing films are pulled away and removed from the package so as to release content of the first and second wells.

According to this non-limiting embodiment, inner diameter A of first well 110 that is configured for holding antagonist bacteria may be 80-300 mm, and at times within the range between 100 mm-200 mm, or 120-150 mm. Inner diameter B of second wells 130 which are configured to hold the same or different bacteria antagonist, is in the range of 20-40 mm, at times within the range between 25-35 mm. The wells have typically a depth of 20-60 mm, at times in the range of 20-30 mm.

In some embodiments, the total dimensions of the package are 500-550 mm length, and 30-40 mm width.

Figure 1B:
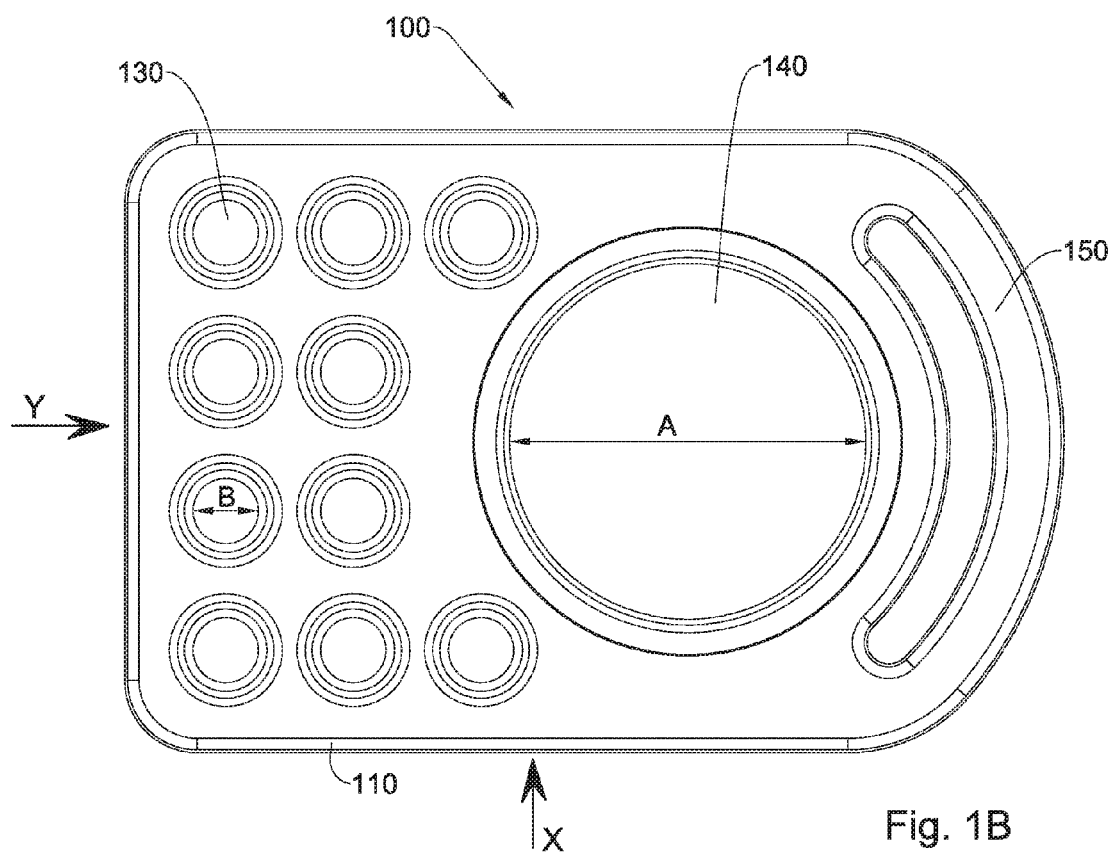
Figure 1C:
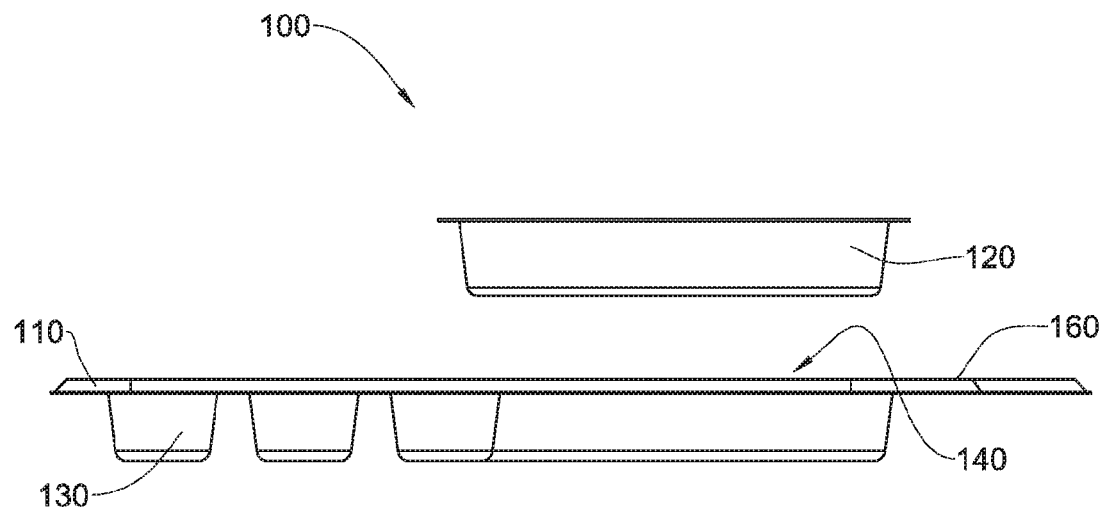
Figure 1D:
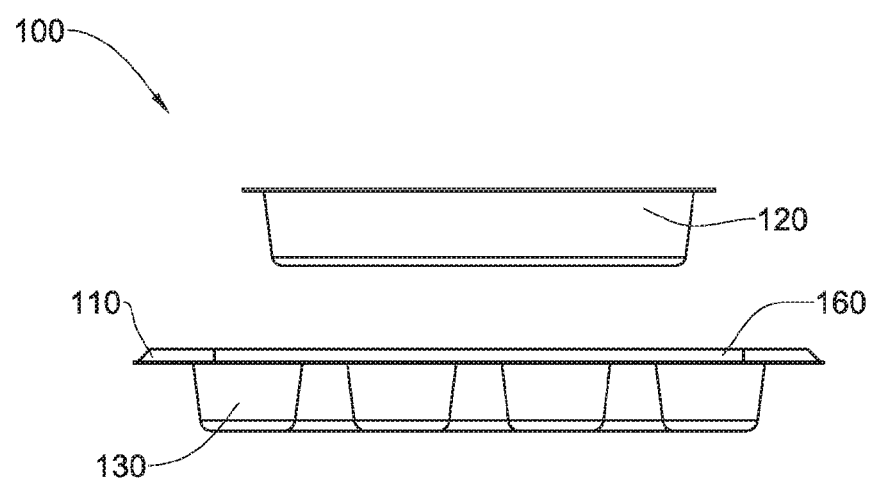

FIGS. 1C, which is view of FIG. 1B also shows depression (recess or holding well) 140 for holding first well 120, depression 140 extending downwardly with respect to top side 160 of the carrier element. FIG. 1D is another view of element 100 from side Y of FIG. 1B.

Figure 2A:
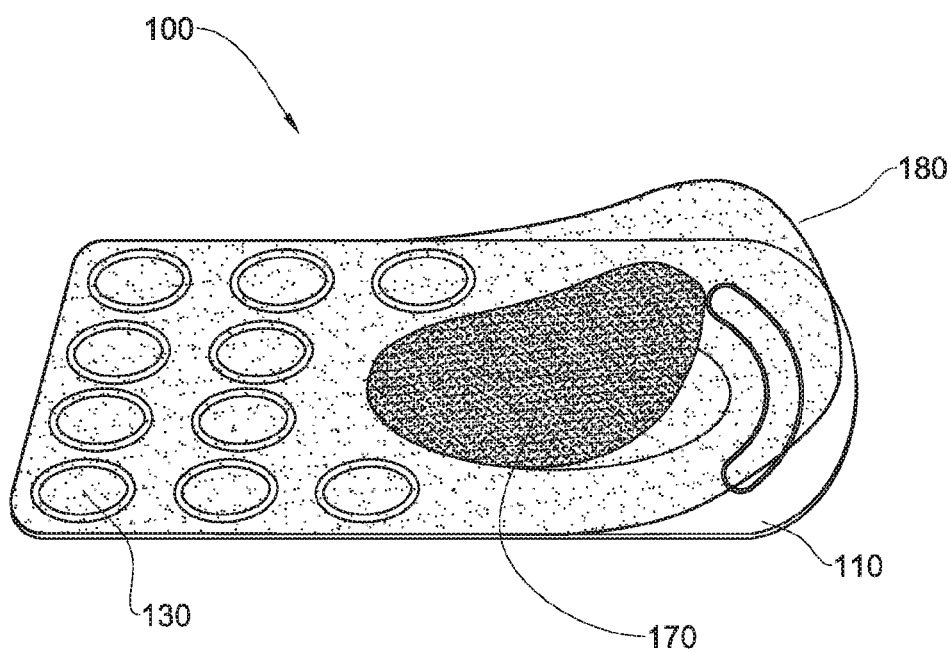
FIGS. 2A-2B show views of a carrier element in accordance with FIGS. 1A-1D, including films sealing the different wells of the carrier element, in accordance with an embodiment of the invention.
Figure 2B:
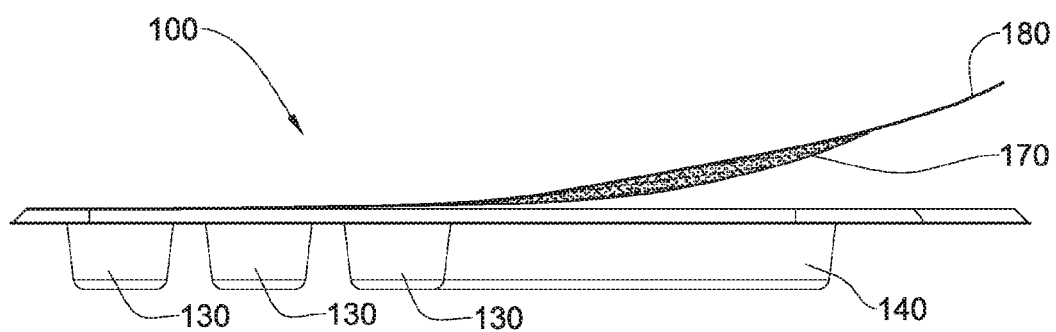

The first film and the second film may each separately cover and seal the respective first wells and second wells. In accordance with some embodiments, and as also illustrated in FIGS. 2A and 2B, carrier element 100 as illustrated in FIGS. 1A to 1D, is combined with a first film 170 partially covering the opening of first well 120 and a second film 180 superimposed over first film 170 and covering (sealing) second wells 130. The first film 170 and the second film 180 may be fixedly attached to each other such that upon pulling away second film 180, the first film 170 is also pulled, thus allowing the opening of first wells 120 and second wells 130 essentially simultaneously. However, in a similar manner, first film 170 may be separate from second film 180 to allow independent opening of the first wells 120 and second wells 130.

Turning now to FIGS. 3A-3E there is provided an element for use in a package in accordance with another embodiment of the present disclosure. Therefore, for simplicity, like reference numerals to those used in FIGS. 1A-1D, shifted by 100 are used to identify components having a similar function in FIGS. 3A-to 3E. For example, component 110 in FIG. 1A is a well having the same function as well 210 in FIG. 2A.

Figure 3A:
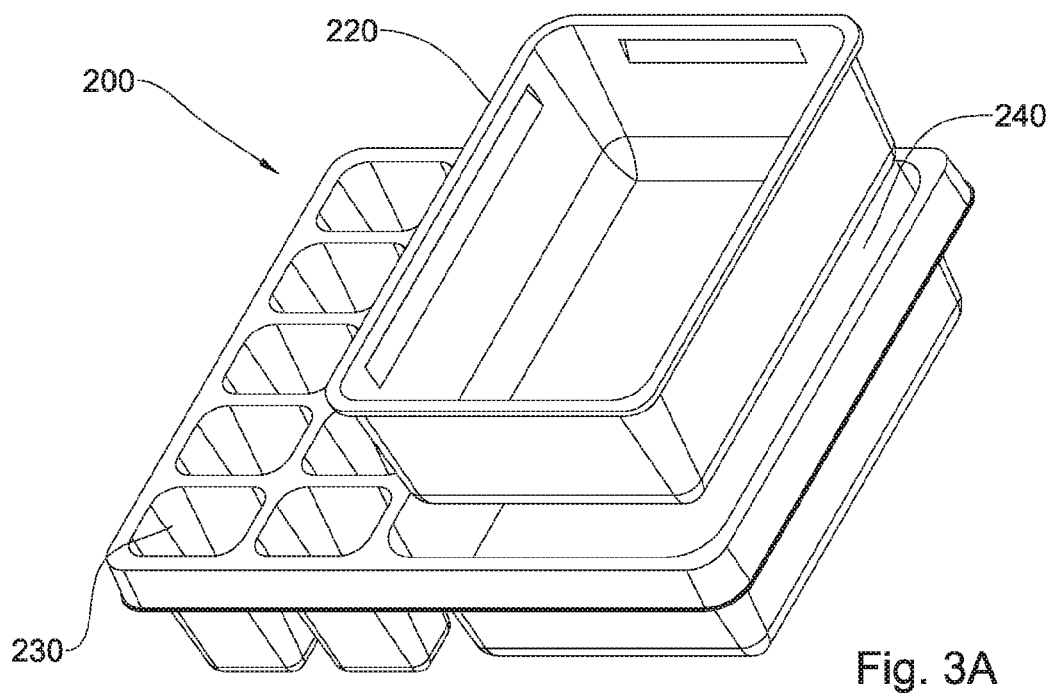
FIGS. 3A-3E show a carrier element according to an embodiment of the invention, from different views with FIG. 3A providing an isometric view, FIG. 3B providing a top view and FIGS. 3C, 3D and 3E, providing views from sides Z, X and Y of FIG. 3B.
Figure 3B:
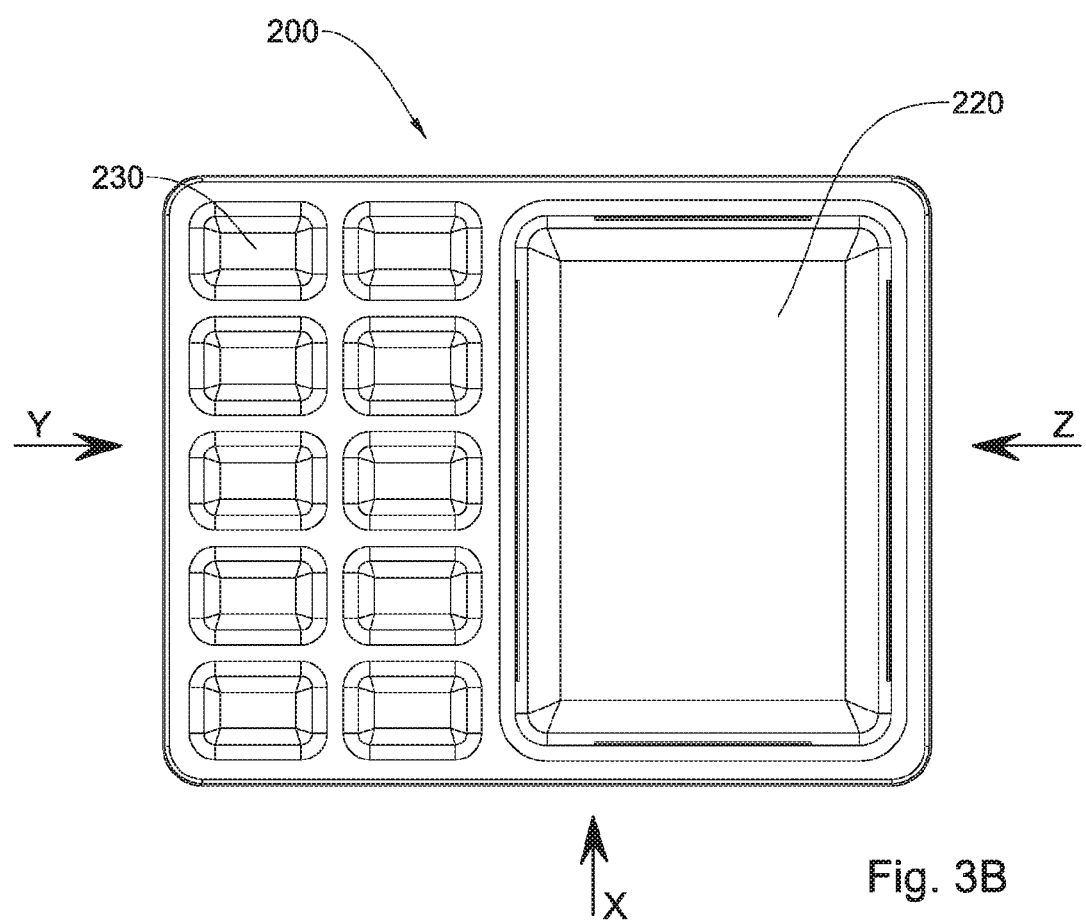
Figure 3C:
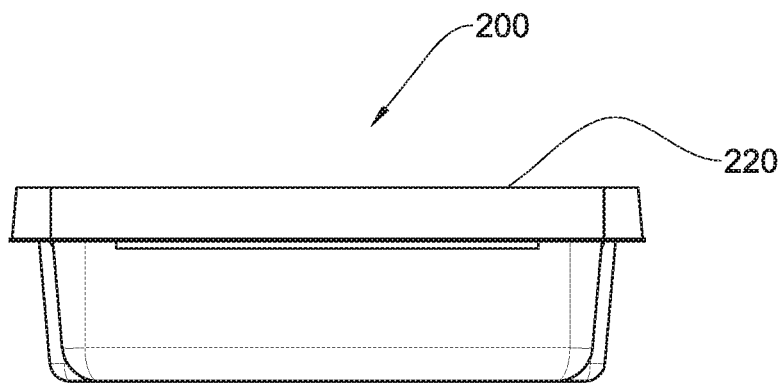
Figure 3D:
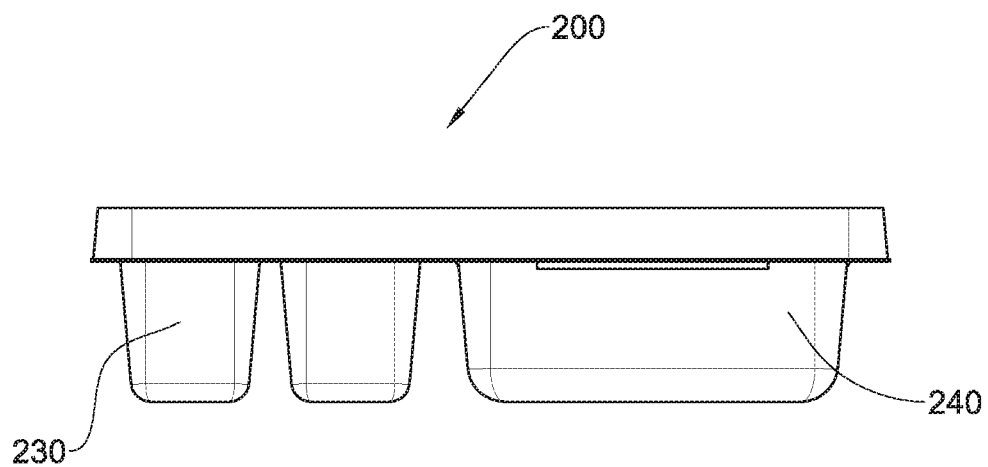
Figure 3E:
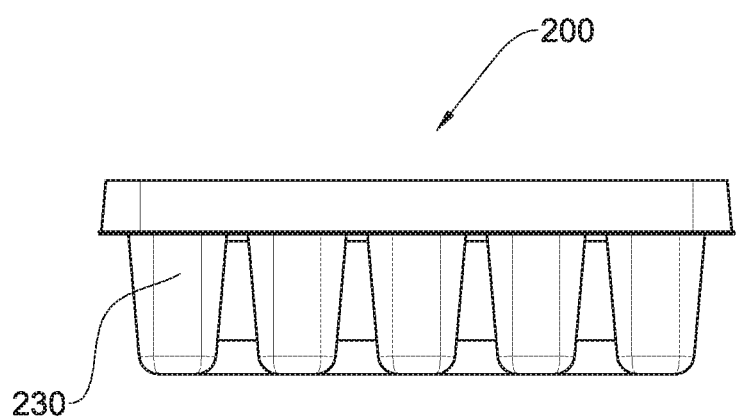

Specifically, FIG. 2A is an isometric view, FIG. 3B is a top view and FIGS. 3C to 3E are side views of an element 200 from sides Z, X and Y, the element 200 having a general oblong (rectangular) shape, with the planar matrix 210 including a single first well 220, being reversibly mountable in a depression 240 provided in planar matrix 210 and a plurality of, spaced apart, second wells 230. In accordance with this non-limiting embodiment, the first well 220 and the second wells 230 are polygonal in shape, in this particular embodiment, quadrilateral.

Further, in accordance with this non-limiting embodiment, second well 230 is shown as an integral part of the carrier element 200 but it may equally be a releasable well, as shown in the non-limiting example of FIG. 1A.

The dimensions of carrier element in accordance with this embodiment may be different from that provided with respect to element 100, and in this particular embodiment may have total dimensions of 200-300 mm length, and 150-250 mm width, with the wells being deeper, i.e. having a depth in the range of between 50-60 nm.

As appreciated, the dimensions of the carrier element and in particular the wells provided thereby may vary depending on the particular application of the package and the material to be carried thereby. Those skilled in the art would readily appreciate the adaptations required in the dimensions in order to fit the carrier to the particular application.

As detailed above, the first well(s) of the package in accordance with the present disclosure holds a composition of matter containing oil. As such at least the one or more first wells are formed from oil compatible polymers. When referring to oil compatible polymers it is to be understood as referring to polymers that are inert and do not change the properties of the composite material including the natural oil. For the same reason, the first film covering the first well(s) is composed of oil compatible polymer.

In some embodiments, the first film of the respective first wells is or comprises oil compatible thermoplastic polymers.

In some embodiments, it is required to maintain the composite material in dry form. To this end, the first film is a fluid impermeable polymer. This are referred to in the art as high barrier (HB) films. HB films may be defined by permeability to $H_2O$ in the range of 3-4 $g/m^3/24$ hr and permeability to $O_2$ in the range of 6-8 $cm^3/m^2/24$ hr.

Some non-limiting examples of HB polymers that may form the first film are those derived from any one of polyolefins, polyvinyls, polyesters.

The HB film is typically of a type that can easily peel-off the carrier.

In some embodiments, the first sealing film is a laminate having a thickness in the range of 40-100 μm, at times, between 60-80 μm.

Turning to the one or more second wells, in accordance with some embodiments, since the second wells carry living matter, it is desirable that the sealing film of these second wells, namely, the second film, be gas permeable. In accordance with some embodiment, the second film is permeable to oxygen or oxygen containing gas. To this end, the permeability of the second film to $H_2O$ may be in the range of 8-10 $g/m^3/24$ hr and permeability to $O_2$ of about 1,200 $cm^3/m^2/24$ hr.

The first and second films may be comprised of thermoplastic films comprising a single or blends of polymers selected from the group consisting of biaxially-oriented polyethylene terephthalate (BOPET), biaxially oriented polypropylene (BOPP), polyvinylidene chloride (PVDC), polyethylene polypropylene, polyvinyl alcohol.

In some embodiments, the films comprise a biaxial oriented polypropylene (BOPP). In some other embodiments, the films are a laminate of BOPP with another polymer, such as polyethylene (PE). The laminate may comprise two, three of more laminated layers. The films to be used are commercially available, e.g. from Glob-Plast (Plastart, Israel) and widely used in the art.

The present disclosure also provides a method of providing a composition for treating or prevention of a pathogen infection in a plant, the method comprise mixing a first component comprising particulate matter comprising at least one natural oil, with a second component comprising at least one antagonist of a microbial pathogen, and allowing said mixture to form into an emulsion. The resulting emulsion may be referred to herein as an anti-microbial (e.g. bactericidal, fungicidal etc) effective emulsion.

In accordance with this method aspect, the first component and the second component are as defined herein.

Mixing may also require the addition of water to form the emulsion. In some embodiments, the mixing provides an emulsion with a droplet size in the range of between 1 to 20 μm and in some embodiments in the range between 3 to 10 μm.

The present disclosure also provides a method of treating or preventing a pathogen infection in a plant, the method comprises applying to said plant an amount of an emulsion comprising particulate matter, at least one natural oil and at least one antagonist of a microbial pathogen. In accordance with this aspect of the present disclosure, the emulsion is obtained by mixing, preferably closely prior to application, a first component and a second component as defined herein.

In some embodiments, the method of treatment or prevention comprises applying the emulsion onto a plant. The application of the emulsion may be by any means known in agriculture, including, without being limited thereto, spraying the plant, irrigation.

In yet some other embodiments, the treatment or prevention may include application onto the plant tubers, such as spraying of potato tubers (at times referred to as low spraying of tubers).

The emulsion may be applied to the plant once to obtain the anti-microbial effect, or two or more times. When more than one dose is applied, the doses may be provided with time intervals between applications of between one day interval to more than one day (two, three and more days interval). The different doses may be the same or different in the amount of the antagonists, the amount of the natural oil or both, as well as the same or different in the type of antagonists and/or natural oils provided.

In some embodiments, when more than one dose is applied, the various applications are in intervals of between 2 to 10 days at times between 3 to 8 days.

In some embodiments, the plant is provided with at least 2, 3, 4, and at times at least 5 doses of emulsion(s) provided in accordance with the present disclosure.

The frequency of treatment and the amount of doses depends on the type of the infection (e.g. how violent/harmful/death threading it is), the severity of infection, if already developed, the environmental conditions, etc. Those versed in agriculture would be able to determine the treatment schedule based on commonly used parameters.

For preventing an infection from development, it is required, in accordance with some embodiments, to apply the emulsion to the plant from the day of planting of the plant or from a first day of a suspected infection.

For treatment of an infection, it is required, in accordance with some embodiments, to apply the emulsion to the plant from the day of detection of a suspected infection.

The present disclosure also provides for an isolated antagonistic bacterium selected from the group consisting of *Pseudomonas* species (Accession No. CBS133252), *Pseudomonas alcaliphila* (Accession No. CBS133254), *Bacillus subtilis* (Accession No. CBS133255), *Pseudomonas cedrina* (Accession No. CBS133256), *Pseudomonas* species (Accession No. CBS133257), *Pseudomonas* species (Accession No.CBS133258), *Pseudomonas* species (Accession No. CBS134568), *Pseudomonas spanius* (Accession No. CBS133259), *Pseudomonas mediterranea* (Accession No. CBS134566), *Pseudomonas chlororahis* (Accession No. CBS134567) and *Pseudomonas* species (Accession No. CBS134568).

In some embodiments, the isolated antagonistic bacterium is within a carrier. In some embodiments, the carrier is a gel or gel-like carrier as defined hereinabove.

The isolated bacterium may have various applications. In some embodiments, the isolated bacterium, alone, or as a bacterial cocktail may be used for treating or protecting plant against a disease caused by a pathogen, such as those disclosed hereinabove. The following are some non-limiting examples for performing the invention. As will be shown, the formulations for the control of plant diseases the oils ingredients and the ratio among the sesame oil or its substitutes and oregano oil and its substitutes are about constant (1:0.25(w/w) ratio of oregano oil:sesame oil) whereas the quantities of the other supplemented to the oils formulation are changed according to the plant, pest and the environmental conditions. At least one antagonistic bacterium out of the possible bacteria is in use in combination with the oils formulation for the control of plant diseases.

DESCRIPTION OF NON-LIMITING EXAMPLES

The study consisted of three parts: (i) isolation and multiplication of the pathogens and potential antagonists; (ii) in vitro screening of potential antagonists against *Clavibacter michiganensis* subsp. *Michiganensis* (CBM), and (iii) in vivo evaluation of selected antagonists for the control of bacterial wilt disease on tomatoes.

Isolating of Pathogens and Potential Antagonistic Bacterial Strains

Tomato plants (Daniela, Hazera, Israel) were grown in greenhouses in double rows of plants on each bed with a drip irrigation system. The seedlings were planted in about 3 plants per meter row and were cultivated according the Dutch (Holland) method. The plots were under surveillance for development of infection by CBM. Upon infection, plants that survived the infection were identified, and samples containing root parts, soil (at depth of 30cm) and the rhizosphere were taken into sterile bags and transported to the laboratory.

In the laboratory, samples of 10 grams each containing root parts, soil, and the rhizosphere were introduce into a stomacher bag containing 90 ml of agar solution 0.1% w/v (diluted with double distilled water (DDW), sealed and sterilized in an autoclave 121° C., 1 atm, 20minutes). Following sterilization, the samples were shaked for 2 hours at a speed of 20 rpm and room temperature. Then, the bags were transferred into a stomacher device for 1 minute, at medium speed.

After stomaching the samples, each bag was opened by sterile scissors, and various dilutions of the samples were prepared in sterile tubes containing each 9 ml of agar solution (0.1% w/v). The first dilution was 1 ml sample into 9 ml agar ($\times 10^{-2}$ dilution), and continued up to $\times 10^{-8}$ dilution.

From each diluted sample, 100 µl were transferred into Petri dishes supplemented with a media selected from one of the following agars: potato dextrose agar (PDA, Difco), a Nutrient Agar, *Pseudomonas* agar F (Difco) and incubated in an incubator (28° C.) for 5 days. Those of interest colonies were marked and transferred using a bacterial needle into a fresh medium (the same as used for growing before isolation) to obtain an isolated single type of microbial colonies of potential antagonists.

Multiplication of Isolated Antagonists

The microbial colonies suspected of having antagonistic effects were purified from the microorganisms growing on the agar plates under a laminar flow hood and re-cultured in *Erlenmeyer flaskon* in a culturing broth containing peptone (10 gr/liter), yeast extract (20 gr/liter), glycerol (10 gr/liter), $MgSO_4$ (0.1 gr/liter), $CaCO_3$ (2 gr/liter), Each flaskon received a single isolated colony for cultivation as a pure antagonist and each flaskon was covered with a plastic cap, sterilized in an autoclave for 20 min at 121° C., and kept at room temperature for one day.

Screening of Effective Antagonists of CBM and/or *Xanthromonas*.

Cultures showing antagonistic activity were screened for effective in vitro suppression of the pathogen by transferring each of the suspected antagonist using a bacterial needle into a Petri dish containing NA medium (nutrient Agar medium), supplemented with 0.1% yeast extract and 1% glycerol. The bacteria were placed on a straight line on the dish and the dish was then incubated for 24 hours at 28° C. After incubation time, CBM pathogen was seeded on an imaginary line perpendicular to the bacteria line and the dish was returned to incubation for an additional period of 3 days. If the bacteria has antagonistic activity, a gap between the bacterial line and the pathogen line was formed during the incubation days those having the greater gap formed, were selected as potential antagonists. These were further identified by the center of Centraalbureau voor Schimmelcultures (Fungal Biodiversity Centre, Institute of Royal Netherlands Academy of Arts and Science (CBS-KNAW).

Table 1 provides the list of species deposited at the CBS-KNAW institute on Nov. 19, 2012 and used in the final combination/cocktail. The species were stored at −80° C. in a glycerol solution (15%).

TABLE 1

Deposited antagonists

| Antagonist | Accession No. | Name |
|---|---|---|
| Pseudomonas species | CBS133252 | BN12-27A |
| Pseudomonas alcaliphila | CBS133254 | BN12-28 |
| Bacillus subtilis | CBS133255 | BN12-29 |
| Pseudomonas cedrina | CBS133256 | BN12-30 |
| Pseudomonas species | CBS133257 | BN-12-31 |
| Pseudomonas species | CBS133258 | BN12-32 |
| Pseudomonas spanius | CBS133259 | BN12-33 |
| Pseudomonas mediterranea AN1 | CBS134566 | BN13-01 |
| Pseudomonas chlororahis AN10 | CBS134567 | BN13-02 |
| Pseudomonas species AN21 | CBS134568 | BN13-03 |

Figure 4A:
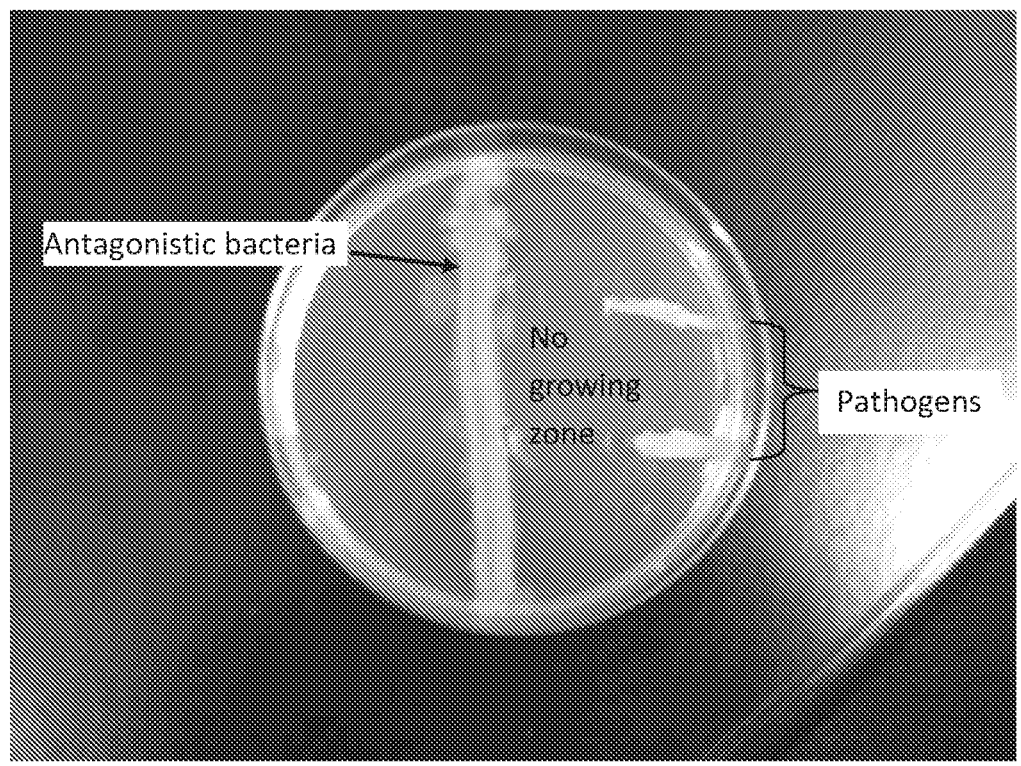
FIG. 4A-4C show the effect of two selected antagonists on growth of CBM (FIG. 4A) and *Xanthromonas* (FIG. 4B) as compared to control (FIG. 4C).
Figure 4B:
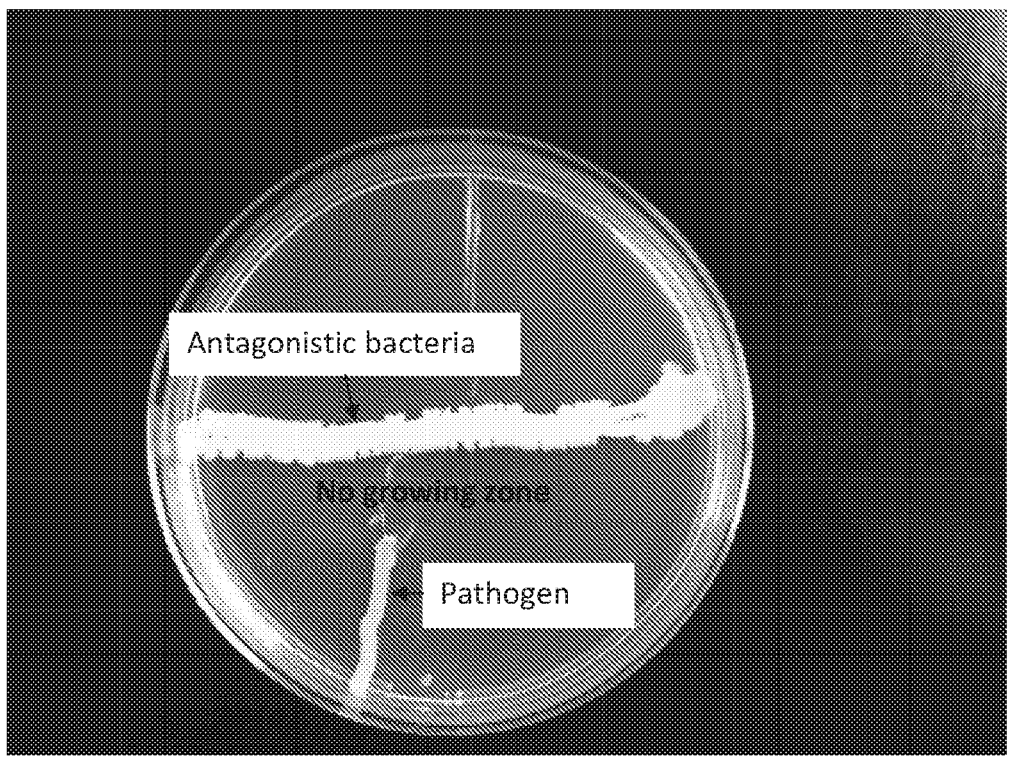
Figure 4C:
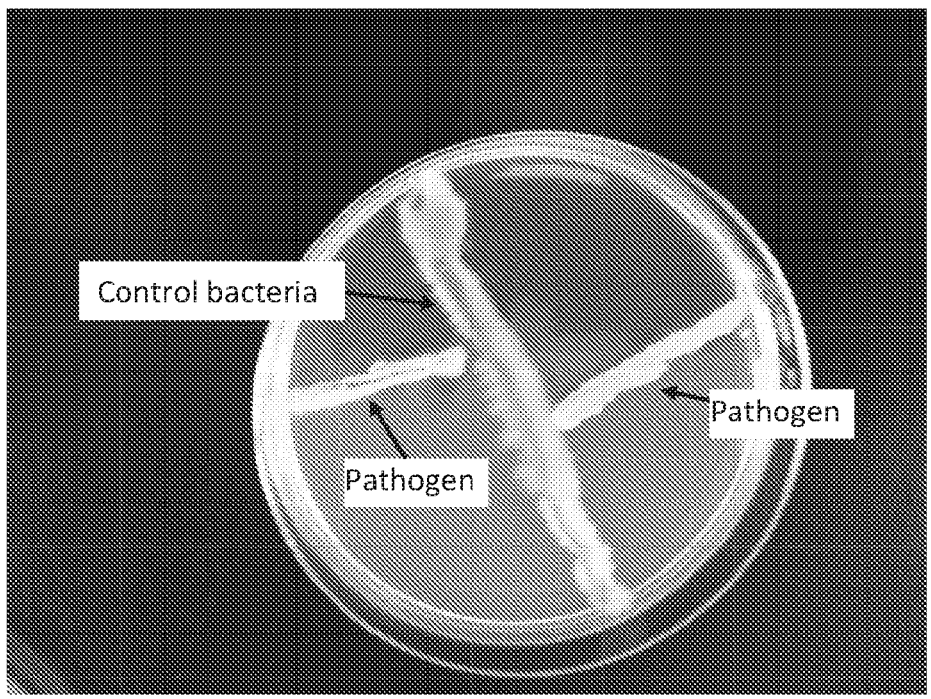
Figure 5A:
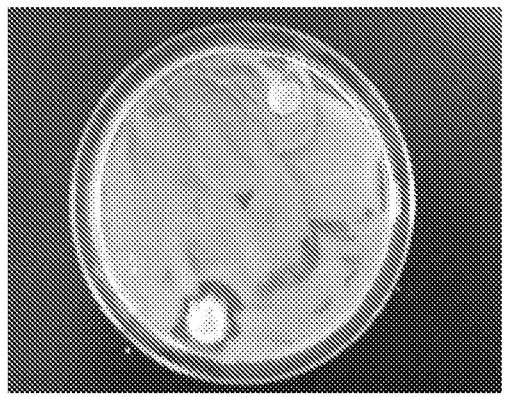
FIGS. 5A to 5E show petri dishes of various pathogens after treatment with a plant pathogen, with or without an antagonistic bacteria
Figure 5B:
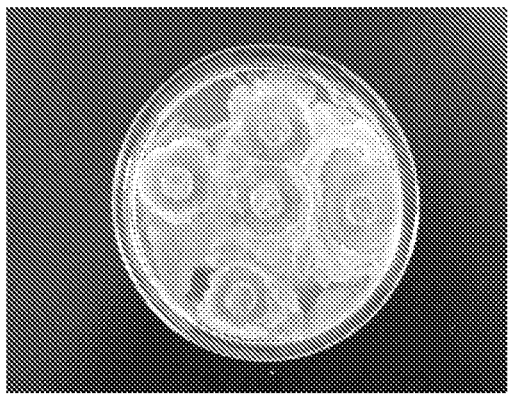
Figure 5C:
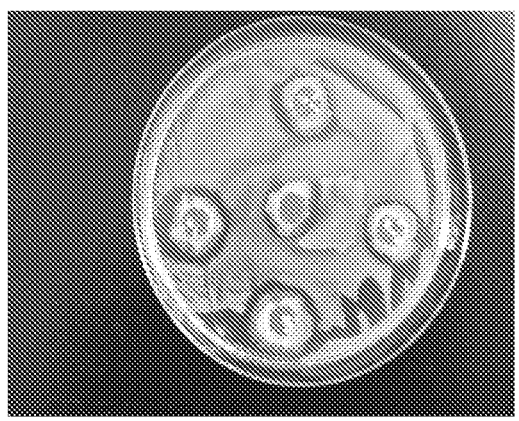
Figure 5D:
Figure 5E:
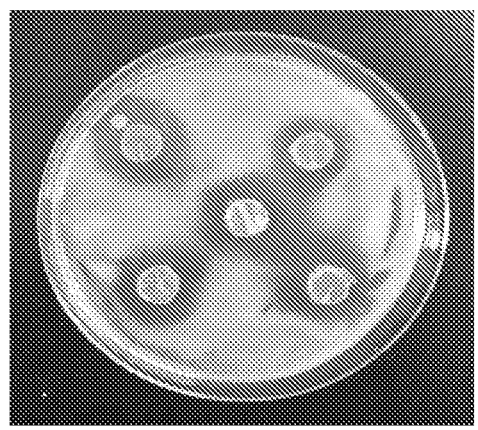

In addition, FIGS. 4A-4C show the effect of antagonists Pseudomonas cedrina (CBS 1333256, "AN4") (FIG. 4A) and Pseudomonas species (CBS 1333258, "AN19") (FIG. 4B) on the growth of CBM and Xanthromonas (two separate spreads/lines on the plate) as compared to the effect of a control being a non-antagonistic bacteria isolated from the same source of the antagonistic bacteria and grown on media without sesame oil (Control bacteria, FIG. 4C). Specifically, in FIG. 4A and FIG. 4B a non-growing zone is shown where the pathogen spreads of CBM and Xanthromonas could not grow towards the antagonistic line. In the control FIG. 4C, the pathogen spreads of CBM and Xanthromonas reached the control bacteria line. These results show that AN4 and AN19 have antagonistic activity towards at least CBM and Xanthromonas.

The same experiment was conducted for each isolated bacteria which led to the list of antagonistic bacteria of Table 1.

Preparing Antagonistic Microbial Gel

Isolated antagonists were separately transferred to Erlenmeyer flask containing the medium used for multiplication (peptone (10 gr/liter), yeast extract (20 gr/liter), glycerol (10 gr/liter), $MgSO_4$ (0.1 gr/liter), $CaCO_3$ (2 gr/liter) supplemented with 0.15% granulated Agar (Difco) and each antagonist at a concentration of between $10^7$ to $10^8$ CFU/ml and shaked for 72 h at 28° C. The resulting gel like cocktail was then kept in gel form, at room temperature until use. It has been shown that the antagonists can be preserved in this form for up to 12 months with a decrease in the bacterial population in logarithmic order of no more than 2.

Determining Media for Maintaining the Antagonist

In order to determine the most appropriate media for storing the antagonistic bacteria, the following possible storage media were tested:

The Tested Antagonistic Bacteria:

The tested antagonistic bacteria were CBS 133252; CBS 133255 and CBS 134567.

Each antagonistic bacteria was grown for 48 h on Petri dishes containing the AN media. The colonies of each bacterium were collected from the surface of the growing media into sterile distilled water to a final concentration of $10^9$ CFU/ml.

The Tested Storage Media:
 a. Distilled water (DW)
 b. Oregano oil 79% and sesame oil 19% and DW 2%.
 c. Oregano oil 4% and sesame oil 0.8% in DW.
 d. An emulsion comprising oregano oil 4%, sesame oil 0.8% in DW+0.05% Tween 80 (surfactant TWEEN® 80(Product Number: P4780 Brand: Sigma).
 e. Antagonistic media ("AN media") as a soft gel comprising yeast extract (20 gr/liter), glycerol (10 gr/liter), $MgSO_4$ (0.1 gr/liter), $CaCO_3$ (2 gr/liter) supplemented with 0.15% granulated Agar (Difco).

Preparing the Storage Media:

Each tested storage media (9 ml) was poured under aseptic condition into 15 ml sterile tubes. In total 120 tubes for each tested storage media.

To each tube, 1 ml of the pre made antagonistic bacteria preparation ($10^9$ cells/ml) was added, were inoculating to each tube to a final concentration of $10^8$ CFU of the tested bacteria in each tube. The inoculated tubes were incubated for a period of 300 days at room temperature around 25° C.

Estimating the Survival of the Tested Bacteria in the Various Storage Media:

During the 294 days of incubation, samples from each tube (5 replications each) were taken periodically. From each tube a tenfold dilution in sterile distilled water was made from 1 to $10^{-8}$. Then, from each dilution, 100 micro liters were spared on the surface AN media. After incubation for 5 days at 25° C., the population was estimated as CFU/ml of the original test tube that were taken at a certain time. The results are the mean of the 5 replications at each time.

Results:

The survival results are summarized in Tables 2A-2E below:

TABLE 2A

Survival of antagonistic bacteria in distilled water

| Days from inoculation | CBS 133252 | CBS133255 | CBS133255 |
|---|---|---|---|
| 1 | $3.1 \times 10^8$ | $2.6 \times 10^8$ | $1.8 \times 10^8$ |
| 14 | $1.6 \times 10^3$ | $1 \times 10^6$ | $4 \times 10^3$ |
| 28 | 40 | $6 \times 10^3$ | 10 |
| 42 | 0 | $2 \times 10^2$ | 0 |
| 56 | 0 | 20 | 0 |
| 70 | 0 | 0 | 0 |
| 84 | 0 | 0 | 0 |
| 98 | — | — | — |
| 112 | — | — | — |
| 126 | — | — | — |
| 140 | — | — | — |
| 154 | — | — | — |
| 168 | — | — | — |
| 189 | — | — | — |
| 210 | — | — | — |
| 231 | — | — | — |
| 252 | — | — | — |
| 273 | — | — | — |
| 294 | — | — | — |

TABLE 2B

Survival of antagonistic bacteria in Oregano oil 79%, sesame oil 19% and DW 2%

| Days from inoculation | CBS 133252 | CBS133255 | CBS133255 |
|---|---|---|---|
| 1 | 6 × 103 | 8.5 × 103 | 1 × 103 |
| 14 | 0 | 20 | 0 |
| 28 | 0 | 0 | 0 |
| 42 | 0 | 0 | 0 |

TABLE 2B-continued

Survival of antagonistic bacteria in Oregano oil 79%, sesame oil 19% and DW 2%

| Days from inoculation | CBS 133252 | CBS133255 | CBS133255 |
|---|---|---|---|
| 56 | — | — | — |
| 70 | — | — | — |
| 84 | — | — | — |
| 98 | — | — | — |
| 112 | — | — | — |
| 126 | — | — | — |
| 140 | — | — | — |
| 154 | — | — | — |
| 168 | — | — | — |
| 189 | — | — | — |
| 210 | — | — | — |
| 231 | — | — | — |
| 252 | — | — | — |
| 273 | — | — | — |
| 294 | — | — | — |

TABLE 2C

Survival of antagonistic bacteria in Oregano oil 4% and sesame oil 0.8% in DW

| Days after inoculation | CBS 133252 | CBS133255 | CBS133255 |
|---|---|---|---|
| 1 | $2.4 \times 10^8$ | $2.5 \times 10^8$ | $1.7 \times 10^3$ |
| 14 | 0 | 10 | 0 |
| 28 | 0 | 0 | 0 |
| 42 | 0 | 0 | 0 |
| 56 | — | — | — |
| 70 | — | — | — |
| 84 | — | — | — |
| 98 | — | — | — |
| 112 | — | — | — |
| 126 | — | — | — |
| 140 | — | — | — |
| 154 | — | — | — |
| 168 | — | — | — |
| 189 | — | — | — |
| 210 | — | — | — |
| 231 | — | — | — |
| 252 | — | — | — |
| 273 | — | — | — |
| 294 | — | — | — |

TABLE 2D

Survival of antagonistic bacteria in an emulsion (oregano oil 4%, sesame oil 0.8% in DW + 0.05% Tween 80)

| Days after inoculation | CBS 133252 | CBS133255 | CBS133255 |
|---|---|---|---|
| 1 | $2 \times 10^8$ | $3 \times 10^8$ | $2 \times 10^8$ |
| 14 | 0 | 30 | 0 |
| 28 | 0 | 10 | 0 |
| 42 | 0 | 0 | 0 |
| 56 | 0 | 0 | 0 |
| 70 | 0 | 0 | 0 |
| 84 | — | — | — |
| 98 | — | — | — |
| 112 | — | — | — |
| 126 | — | — | — |
| 140 | — | — | — |
| 154 | — | — | — |
| 168 | — | — | — |
| 189 | — | — | — |
| 210 | — | — | — |
| 231 | — | — | — |
| 252 | — | — | — |
| 273 | — | — | — |
| 294 | — | — | — |

TABLE 2E

Survival of antagonistic bacteria in gel (yeast extract, glycerol, MgSO$_4$, CaCO$_3$, granulated Agar)

| Days after inoculation | CBS 133252 | CBS133255 | CBS133255 |
|---|---|---|---|
| 1 | $3.2 \times 10^8$ | $2.6 \times 10^8$ | $1.9 \times 10^8$ |
| 14 | $3.6 \times 10^8$ | $3.0 \times 10^8$ | $1.6 \times 10^8$ |
| 28 | $3.5 \times 10^8$ | $3.0 \times 10^8$ | $1.5 \times 10^8$ |
| 42 | $3.6 \times 10^8$ | $3.0 \times 10^8$ | $1.6 \times 10^8$ |
| 56 | $3.5 \times 10^8$ | $2.6 \times 10^8$ | $1.5 \times 10^8$ |
| 70 | $4.2 \times 10^7$ | $2.2 \times 10^8$ | $3.5 \times 10^7$ |
| 84 | $1.0 \times 10^7$ | $1.0 \times 10^8$ | $1.0 \times 10^7$ |
| 98 | $3.0 \times 10^6$ | $3.3 \times 10^7$ | $1.0 \times 10^6$ |
| 112 | $3.0 \times 10^6$ | $3.0 \times 10^7$ | $1.0 \times 10^6$ |
| 126 | $4.0 \times 10^6$ | $4.0 \times 10^7$ | $9.0 \times 10^5$ |
| 140 | $8.0 \times 10^5$ | $9.3 \times 10^6$ | $6.0 \times 10^5$ |
| 154 | $8.0 \times 10^5$ | $8.8 \times 10^6$ | $4.0 \times 10^5$ |
| 168 | $6.0 \times 10^5$ | $6.0 \times 10^6$ | $5.0 \times 10^5$ |
| 189 | $3.0 \times 10^5$ | $3.0 \times 10^6$ | $1.0 \times 10^5$ |
| 210 | $1.0 \times 10^5$ | $9.0 \times 10^5$ | $1.0 \times 10^5$ |
| 231 | $8.0 \times 10^4$ | $8.1 \times 10^5$ | $6.1 \times 10^4$ |
| 252 | $7.4 \times 10^4$ | $8.1 \times 10^5$ | $7.4 \times 10^4$ |
| 273 | $7.6 \times 10^4$ | $8.1 \times 10^5$ | $6.4 \times 10^4$ |
| 294 | $7.6 \times 10^4$ | $8.1 \times 10^5$ | $5.8 \times 10^4$ |

Specifically, the results presented in Tables 2A to 2E show that the survival of the three tested antagonistic bacteria in the four first tested storage media was significantly different from the gel based media.

Specifically, only the gel (agar containing) media supported the long term (294 days) survival of the antagonistic bacteria. At the end of the experiment the population of CBS 133252 and CBS 133255 was above $5.0 \times 10^4$ CFU/ml, while CBS 133255 survived to a level of about $8.0 \times 10^5$. In all other tested media the antagonistic bacteria did not survive after the about 40 days.

Further Characterization of Antagonistic Bacteria

To further characterize the antagonistic bacteria, the difference in growth of the bacterial (as well as non-antagonists) on various carbon source material has been investigated. Specifically, the growth of 10 antagonistic bacteria and 6 non-antagonistic bacteria on sesame oil, glucose or glycerol as separate carbon sources was examined. A media without carbon source was used as the control.

Materials

The growth media included:

| | |
|---|---|
| Distilled water | 500 ml |
| NH$_4$H$_2$PO$_4$ | 0.10 gr |
| MgSO$_4$*7H$_2$O | 0.01 gr |
| KCl | 0.10 gr |
| Tested carbon source | 4.20 gr |

The Bacteria Stock Solution Included:

The bacteria was collected from 24 h bacterial culture from which a solution of 0.65 Absorbance at 480 nm, diluted 1:100 with distilled water was prepared.

Method

Ten milliliters of the growth media with or without the tested carbon source was poured into 30 ml Erlenmeyer flasks and inoculated with 100 μl of the selected bacterial solution. The inoculated flasks were incubated at 26° C., for 24 h and then subjected to a ten-fold dilution and counted. Water was used as control.

Table 3 provides the colony forming units/ml for each texted carbon source and bacteria. In Table 3, the isolated and deposited bacteria from Table 1 were compared with bacteria isolated from the soil as described above, but found to have no antagonistic activity, these being referred to as *Pseudomonas* spp 12 (*P.* spp 12), *Pseudomonas* spp 13 (*P.* spp 13), *Pseudomonas* spp 14 (*P.* spp 14), *Pseudomonas* spp 15 (*P.* spp 15), *Bacilus* spp 36, *E. coli* 4.

The results in Table 3 show that bacteria with no identified antagonistic activity were not able to grow on sesame oil as a sole carbon source.

TABLE 3

Bacterial growth

| Bacteria deposit number | Control* | Sesame oil | Glucose | Glycerol |
|---|---|---|---|---|
| CBS134566 | 60 | $5 \times 10^8$ | $10^7$ | $2 \times 10^9$ |
| CBS133252 | 80 | $3 \times 10^8$ | $10^2$ | $4 \times 10^8$ |
| CBS133254 | 100 | $1 \times 10^9$ | $6 \times 10^2$ | $1 \times 10^9$ |
| CBS133255 | 50 | $6 \times 10^8$ | $7 \times 10^2$ | $7 \times 10^8$ |
| CBS133256 | 110 | $9 \times 10^7$ | $6 \times 10^8$ | $5 \times 10^8$ |
| CBS134567 | 90 | $3 \times 10^8$ | $1 \times 10^9$ | $5 \times 10^8$ |
| CBS133257 | 130 | $2 \times 10^9$ | 120 | $4 \times 10^9$ |
| CBS133258 | 140 | $7 \times 10^7$ | 156 | $1 \times 10^8$ |
| CBS133259 | 60 | $1 \times 10^8$ | 150 | $1 \times 10^8$ |
| CBS134568 | 70 | $6 \times 10^7$ | $3 \times 10^8$ | $7 \times 10^7$ |
| P. spp 12 | 60 | 75 | $4 \times 10^9$ | $8 \times 10^8$ |
| P. spp 13 | 70 | 54 | $3 \times 10^8$ | $1 \times 10^8$ |
| P. spp 14 | 90 | 100 | $8 \times 10^8$ | $5 \times 10^8$ |
| P. spp 15 | 90 | 86 | $3 \times 10^9$ | $6 \times 10^8$ |
| *Bacilus* spp 36 | 90 | 100 | $3 \times 10^9$ | $7 \times 10^8$ |
| *E. coli* 4 | 110 | 98 | $8 \times 10^8$ | $4 \times 10^8$ |
| Water | | 0 | 0 | 0 |

Verifying Anti-Bacterial Effect of Essential Oils

Materials and Methods

To verify the anti-bacterial effect of essential oil, the following assay was conducted.

Oil: Oregano oil with the following particulars: country of origin: Bulgaria; plant parts: flowering plant; cultivation method: certified organics, method of extraction: steam distilled.

Bacterial strains: *Escherichia coli, Staphylococcus aureus, Salmonella, Clavibacter* and *Xanthomonas campestris* were obtained from the collection of Prof. G. Kritzman Israel.

Disc Diffusion method: Bacteria were grown in nutrient broth test tubes at 27° C. for 24 hrs. The paper discs were sterilized by autoclave in preparation for the disc diffusion method. Each bacteria (100 µl), was placed on Nutrient agar (NA) plates and allowed to dry for 3-5 minutes. The paper discs were saturated in 100% concentration of the oregano essential oil (20 ul), and then placed onto each NA plate freshly coated with bacteria. The positive control used was 3% $H_2O_2$ solution and the negative control was DI water. The plates were incubated at 27° C. for 48 hours. The zone of inhibition was measured by standard ruler.

Results

The anti-bacterial effect of the commercial organic oils on bacteria is summarized in Table 4, showing a greater inhibition zone for the oregano oils treated bacteria as compared to the controls.

TABLE 4

Anti-bacterial effect of oregano oil

| The tested bacteria | Inhibition zone (mm) |
|---|---|
| *E. coli* | 15 |
| *S. aureus* | 19 |
| *Salmonela* | 21 |
| *Clavibacter* | 24 |
| *Xanthomonas campestris* | 22 |
| Positive control | 8 |
| Negative control | 0 |

Preparation of Essential Oil Powder

Materials

For preparing the oil powder, the following materials were used:

Natural oils:

Oregano oil 100% (essential oil) and Sesame oil 100% (carbon-base oil), both purchased from Makes Scents Natural SPA line, Lancaster Pa., USA.

Surfactants:

Thymol, Carvacrol, Tween80, Tween 65, Tween R85 and Egg Lecithin all purchased from Sigma-Aldrich.

Span 40 purchased from Fluka, Israel.

Zohar LQ-215 (Potassium fatty acids) and Zohar PT-50 (Potassium fatty acids) purchased from Zohar Dalia.

Silica beads:

Tixosil ($SiO_2$) purchased from Rhodia group.

Aerosil 200 and Sipernat 50S ($SiO_2$, 20 µm) purchased from Evonik Industries AG.

Solvent:

Acetone and Acetonitrile purchased from J. T. Becker, Isopropanol (IPA), Gadot.

Methods

Powder Preparation

For laboratory scale production the powders containing the natural oils, surfactants and the silica beads were prepared using common lab glassware set up including laboratory bottles of 20-50 ml sizes, spatulas, magnetic stirrers and heating plates. Generally, the natural oil was weight and each was separately mixed with the selected surfactant in a 20 ml vial, to which the solvent was added. The mixture of each oil were mixed and heated to a temperature of about 40° C. until homogeneous solutions were obtained. To the homogenous solutions the silica beads were added until the liquid was absorbed by the beads. The bottles were left in the fuming hood overnight until all solvent has evaporated.

Loading of each of the oil in the final dry powders was 30-42%. The dry powders contained 2%-7% water.

All ratios of ingredients for powders preparation are provided in Tables 5A-5D:

TABLE 5A

Oregano oil based powder

| Form. No. | Oregano oil | Surfactant | | | | | Silica beads | | Solvent |
| --- | --- | --- | --- | --- | --- | --- | --- | --- | --- |
| | | Tween 80 | Lecithin | Tween 85 | Tween 65 | Span 40 | Tixosil | Aerosil 200 | Acetone |
| ORG-18A | 0.5 g | 0.5 g | 0.1 g | | | | | 0.8 g | 1 g |
| ORG-18B | 0.5 g | 0.5 g | | | | 0.1 g | | 0.8 g | 1 g |
| ORG-18C | 0.5 g | 0.5 g | | 0.1 g | | | | 0.8 g | 1 g |
| ORG-18D | 0.5 gg | 0.5 g | | | 0.1 g | | | 0.8 g | 1 g |
| ORG-20C | 0.5 g | 0.5 g | | | 0.1 g | | 0.56 g | 0.24 g | 1 g |
| ORG-20D | 0.5 g | 0.5 g | | | 0.1 g | | 0.4 g | 0.4 g | 1 g |

TABLE 5B

Sesame oil based powder

| Form. No. | Sesame oil | Surfactant | | | | | Silica beads | | Solvent |
| --- | --- | --- | --- | --- | --- | --- | --- | --- | --- |
| | | Tween 80 | Lecithin | Tween 85 | Tween 65 | Span 40 | Tixosil | Aerosil 200 | Acetone |
| SES-19A | 0.5 g | 0.5 g | 0.1 g | | | | | 0.8 g | 1 g |
| SES-19B | 0.5 g | 0.5 g | | | | 0.1 g | | 0.8 g | 1 g |
| SES-19C | 0.5 g | 0.5 g | | 0.1 g | | | | 0.8 g | 1 g |
| SES-19D | 0.5 gg | 0.5 g | | | 0.1 g | | | 0.8 g | 1 g |
| ORG-21C | 0.5 g | 0.5 g | | | 0.1 g | | 0.56 g | 0.24 g | 1 g |
| ORG-21D | 0.5 g | 0.5 g | | | 0.1 g | | 0.4 g | 0.4 g | 1 g |

TABLE 5C

Self emulsified Oregano oil based powder using anionic surfactants

| Form. No. | Oregano oil | Surfactant | | Silica beads | | Solvent | |
| --- | --- | --- | --- | --- | --- | --- | --- |
| | | Zohar PT-50 | Zohar LQ 215 | Tixosil | Aerosil 200 | Isopropyl alcohol | Acetone |
| ORG-22A | 0.5 g | | 0.5 g | 0.56 g | 0.24 g | | 0 |
| ORG-22B | 0.5 g | | 0.5 g | 0.4 g | 0.4 g | | 1 g |
| ORG-24A | 0.5 g | | 0.25 g | 0.4 g | 0.4 g | | 0 |
| ORG-24B | 0.5 g | | 0.25 g | 0.4 g | 0.4 g | | 0.5 g |
| ORG-24C | 0.75 g | | 0.25 g | 0.4 g | 0.4 g | | 1 g |
| ORG-28 | 0.5 g | 0.25 g | | 0.56 | 0.24 g | 1 g | |

TABLE 5D

Self emulsified Sesame oil based powder using anionic surfactants

| Form. No. | Sesame oil | Surfactant | | Silica beads | | Solvent | |
| --- | --- | --- | --- | --- | --- | --- | --- |
| | | Zohar PT-50 | Zohar LQ 215 | Tixosil | Aerosil 200 | Isopropyl alcohol | Acetone |
| ORG-23A | 0.5 g | | 0.5 g | 0.56 g | 0.24 g | | 0 |
| ORG-23B | 0.5 g | | 0.5 g | 0.4 g | 0.4 g | | 1 g |
| ORG-25A | 0.5 g | | 0.25 g | 0.4 g | 0.4 g | | 0 |
| ORG-25B | 0.5 g | | 0.25 g | 0.4 g | 0.4 g | | 0.5 g |
| ORG-25C | 0.75 g | | 0.25 g | 0.4 g | 0.4 g | | 1 g |
| ORG-29 | 0.5 g | 0.25 g | | 0.56 | 0.24 g | 1 g | |

For greater amounts, laboratory electro-mechanical means similar to those used in the industry were employed. These included:

1. Vertical Mechanical Stirrer DC Hsiangtai equipped with propeller;
2. Peristaltic pump 4.4 Carter ⅘ cassette manostat and tubing;
3. Dynamic Exim 5 L powder mixer equipped with ribbon type mixing blades
4. Balances
5. Beakers 1-2 L and containers 1-3 L The preparation included weighting and mixing the oil with the surfactant(s) in a 1 L beaker, to which isopropyl alcohol was added while mixing until a homogenous solution was obtained. The silica beads (Sipernat 50S) were added to a 2 L beaker to which the homogenous solution was slowly (rate of 10 ml/min) added while mixing (30 rpm) until all liquid was absorbed into the beads.

All ratios of ingredients for powders preparation are provided in Tables 6A and 6B. The loading of the oil in the range of about 30%-42% was maintained.

TABLE 6A

Oregano oil based powder

| Form. No. | Oregano Oil | Surfactant Zohar PT 50 | Silica beads Sipernat 50S | Solvent IPA |
|---|---|---|---|---|
| 33 | 20 g | 10 g | 30 g | 20 g |
| 34 | 200 g | 100 g | 300 g | 200 g |
| 37A | 20 g | 15 g | 30 g | 20 g |
| 37B | 20 g | 10 g | 300 g | 15 g |
| 38 | 2 × 200 g | 2 × 125 g | 2 × 300 g | 2 × 125 g |

TABLE 6B

Oregano oil based powder

| Form. No. | Oregano Oil | Surfactant Zohar PT 50 | Silica beads Sipernat 50S | Solvent IPA |
|---|---|---|---|---|
| 35 | 200 g | 100 g | 300 g | 200 g |
| 39 | 200 g | 125 g | 300 g | 125 g |

In addition, also mixtures of powders (those containing Oregano oil and those containing Sesame oil) were prepared. Specifically, 400 g of formulation ORG-34 (beads carrying oregano oil) was mixed with 100 g of formulation SES-35 (beads carrying Sesame oil) in Dynamic Exim 5 L powder mixer at 10 rpm producing the mix O&S-A.

Each type of oil based powder was dried in the vacuum oven at 40° C. for 24 hr prior to mixing the two populations together.

In a different process, 800 g of formulation ORG-38 was mixed with 200 g of formulation SES-39 in Dynamic Exim 5 L powder mixer at 10 rpm producing the mixed beads formulation O&S-B.

The mixed bead powders were used as is.

Characterization

Determination of Water Content in Powder

Water content was determined using Mettler Toledo DL-38 Karl Fisher titrator according to USP <921> method.

Determination of Isopropanol Content in Powder

IPA content was determined using a headspace analysis according to the parameters below:

| Gas chromatograph | Agilent 7890 A |
|---|---|
| Column | BPX Volatiles, 60 m × 0.25 mm, 1.4 µm, SGE |
| Oven Program | 45° C. for 2 min, then 10° C./min to 100° C., then 25° C./min to 240° C., for 5 min. |
| Split | 1:25 |
| Mass spectrometer | Agilent 5975C |
| Autosampler program | CTC Combi PAL |
| | Pre-incubation time: 300 s |
| | Incubation temp.: 80° C. |
| | Syringe temp: 100° C. |
| | Volume of injection: 500 µl |
| Headspace vial | 20 ml |
| Volume of sample (water) | 2 ml |
| Calibration points (µg/ml) | 10, 25, 100, 500, 1000 |
| Concentration of ISTDs (ethanol) | 50 µg/ml |

Assay of Oregano Oil in Dry Powder using HPLC

Impurities profile were determined in accordance with the method reported by H. Hajimehdipoor "A validated high performance liquid chromatography method for the analysis of thymol and carvacrol in *Thymus vulgaris* L. volatile oil" in Pharmacogn Mag. 2010 July-September; 6(23): 154 158 and adopted by SoluBest. For this purpose Nucleosil 100 C18 HD, 3µ, 150×3 mm column and Ultimate 3000 Dionex (Germany) HPLC system with photodiode array (PDA) detectors and Chromeleon Version 6.80 software packages were used. The mobile phase is Acetonitrile:Water (50:50, v/v). Minimum resolution between Carvacrol and Thymol peaks is 1.5.

Standard solutions were prepared in duplicate as following:

About 3 mg Thymol and 20 mg Carvacrol were weighted into 50 mL volumetric flask, and dissolved in 40 mL of diluents, then brought up to volume with the diluent and mixed. The resulting concentration of the Thymol standard solution was about 0.06 mg/mL and Carvacrol standard solution was about 0.4 mg/mL.

Sample solutions were prepared in duplicate as following:

About 70 mg of powdered sample was weighted into a 25 mL volumetric flask, then brought up to volume with the acetone and mixed.

Assay of Sesame Oil in Formulation using GC

Sesame oil absorbed on silica beads was trans-methylated overnight with methanolic HCl solution at 60° C. Heptadecanoic acid, used as an internal standard, was added to beads before derivatization. Methyl esters of fatty acids were extracted with hexane and dried over anhydrous sodium sulfate prior to GC analysis.

Calibration standards were prepared from different concentrations of sesame oil and blank beads. Conditions of derivatization and amount of internal standard were the same as described in sample preparation.

Quantitative analysis of sesame oil in beads was performed using Agilent 7890 gas chromatograph equipped with FID detector. Compounds were separated on DB-23 capillary column.

Results

Conventional HPLC and GC analytical methods for Oregano and Sesame oils assay were employed.

The chromatograms of the tested powders showed that no degradation (according to the conventional markers, Thymol and Carvacrol aromatic compounds) of the oil was caused during the powder preparation and storage. Table 7 below provides % of Oregano oil and Sesame oil, respectively, in the powder based on Thymol and Carvacrol aromatic compounds analysis by HPLC.

TABLE 7

Oregano oil content in formulations as measured by HPLC

| Form. No | Sample | % via Thymol | % via Carvacrol |
|---|---|---|---|
| ORG-18A | ORG-18A-1 | 25.2 | 27.1 |
| | ORG-18A-2 | 27.1 | 28.3 |
| | Average | 26.1 | 27.7 |
| | Difference, % | 7.2 | 4.3 |
| ORG-28 | ORG-28-1 | 33.8 | 34.9 |
| | ORG-28-2 | 32.1 | 33.2 |

TABLE 7-continued

Oregano oil content in formulations as measured by HPLC

| Form. No | Sample | % via Thymol | % via Carvacrol |
|---|---|---|---|
| | Average | 32.9 | 34.1 |
| | Difference | 5.5 | 5.2 |
| ORG-32 | ORG-32-1 | 28.0 | 30.3 |
| | ORG-32-2 | 28.1 | 30.7 |
| | Average | 28.0 | 30.5 |
| | Difference | 0.6 | 0.7 |
| ORG-34 | ORG-34-1 | 26.9 | 29.8 |
| | ORG-34-2 | 27.7 | 30.1 |
| | Average | 27.3 | 30.0 |
| | Difference | 2.1 | 2.0 |
| ORG-38 | ORG-38-1 | 28.8 | 28.7 |
| | ORG-38-2 | 28.0 | 29.3 |
| | Average | 28.4 | 29.0 |
| | Difference | 4.1 | 2.0 |

Table 8 provides the % of Sesame oil in the formulation as determined by GC Chromatograph.

TABLE 8

Sesame oil content in formulations as measured by GC chromatography

| Form. No. | Sample | % via C16:0 | % via C18:0 | % via C18:2 |
|---|---|---|---|---|
| SES-19A | SES-19A-1 | — | — | 28.0 |
| | SES-19A-2 | — | — | 27.6 |
| | Average | — | — | 27.8 |
| | Difference, % | — | — | 1.4 |
| SES-35 | SES-35-1 | 29.8 | 30.5 | 37.5 |
| | SES-35-2 | 30.6 | 30.6 | 33.4 |
| | Average | 30.2 | 30.6 | 35.5 |
| | Difference, % | 2.6 | 0.3 | 12.3 |
| SES-39 | SES-39-1 | 32.8 | 33.0 | 39.8 |
| | SES-30-2 | 31.5 | 32.3 | 37.4 |
| | Average | 32.2 | 32.7 | 38.6 |
| | Difference, % | 4.1 | 2.2 | 6.4 |

The water content measured using Karl Fisher titration found that the powder contains 5-7% of water. It appears the source of the water is from Zohar PT 50 surfactant, which contents 50% of water.

As to IPA content, GC Headspace precise analysis demonstrate the IPA content in the formulations, which is summarized in Table 9.

TABLE 9

IPA content in the powders

| Form. No | Sample Amount (gr.) | IPA (μg/ml) | IPA (%) |
|---|---|---|---|
| 34 | 19.6 | 1,265 | 12.9 |
| 35 | 200 | 1,139 | 11.4 |

TABLE 9-continued

IPA content in the powders

| Form. No | Sample Amount (gr.) | IPA (μg/ml) | IPA (%) |
|---|---|---|---|
| 38 | 20.3 | 1,117 | 11.0 |
| 39 | 19.8 | 492 | 5.0 |

As can be seen from the Table 9, the amount of IPA varies from 5 to 13%. However, in the field, the formulations were diluted for at least 30 times and as such, the content of IPA was reduced to 0.17-0.43%, which is negligible and very safe amount.

The different types of dry powders prepared showed stable after long term (more than a year) storage. In addition to the above, it is noted that the powders have a characteristic odor. The oregano oil based formulations have off-white color and sesame oil based powders are white.

Upon contact with water tested formulations (ORG-28 and SES-29 immediately form an emulsion, which were stable for 24 h. The emulsions consisted of droplets of 3-10 microns. The spray-ability of the emulsions was good without clogging the filters.

Safety studies in the field showed that the tested oil based powders were safe. This was determined by the presence (or not) of burns on the plants, as determined by conventional phytotoxicty parameters.

Further, long term (8 weeks) stability of the powders was determined. Specifically, the Oregano and Sesame based powders were separately sealed in aluminum foil bags and placed at accelerating storing conditions (40° C. for 8 weeks). Assay of Oregano oil was measured via two major constituents—Carvacrol and Thymol in the beginning of the stability study (initial point) and after 8 weeks using HPLC-UV technique. The obtained values were normalized to the amounts of markers in the pure oregano oil.

Assay of sesame oil was measured via two major constituents—C16:0 and C18:0—in the beginning of the stability study (initial point) and after 8 weeks using GC-FID analysis of methylated fatty acids. Trans methylation was performed upon acidic catalysis (with MeOH/HCl) using C17:0 as an internal standard. The obtained values were normalized to the amounts of markers in the pure sesame oil.

No significant changes were observed in the both formulations: amount of oregano and sesame oils were similar before and after stability studies.

Water content was tested using Karl Fisher method. The amount of water was reduced on 42% after 8 weeks of storing in accelerating conditions in both formulations.

Isopropanol content was tested using GC method. The amount of IPA was reduced on 36% after 8 weeks of storing in accelerating conditions in oregano formulation, but it was preserved in the sesame formulation.

Without being bound by theory, it appears that the containers were leaky and in order to reduce water or IPA loss, the containers may be more hermetically sealed.

Powders stored 8 weeks at 40° C. showed good ability to form a stable emulsion similar to those of the initial powders. The stability measurements are summarized in Table 10 below:

TABLE 10

Stability Assays

|  | Time point | Oregano oil (%) via C16:0 | Oregano oil (%) via C18:0 | Sesame oil (%) via Thymol | Sesame oil (%) via Carvacrol | Water, % | IPA, % |
|---|---|---|---|---|---|---|---|
| Oregano powder SORG-121-38 | Initial | | | 28.4 | 29.0 | 7.05 | 11 |
| | 8 weeks | | | 29.8 | 29.1 | 4.05 | 7 |
| Sesame powder SES-121-39 | Initial | 32.2 | 32.7 | | | 6.65 | 5 |
| | 8 weeks | 33.3 | 34.2 | | | 3.81 | 5 |

Solubilization and Anti-Bacterial Activity with Different Surfactants

In order to create stable oil-in-water emulsion a surfactant (emulsifying agent) with HLB of 8-20 is required. Thus, in the following, two surfactants were tested Tween 80 having an HLB value of 15 and potassium salt of fatty acids extracted from palm, coconut, olive, castor and cottonseed plants (potassium salt oleate having an HLB value of 20).

It has been found that with the potassium salts of fatty acids the ratio of oil/surfactant required for obtaining a stable emulsion of oregano oils is 1:0.4 while with Tween 80, the required oil/surfactant ratio was 1:1.

The correlation between HLB values and solubilization capacity of each surfactant was found in the current case of Oregano oil, i.e. better solubiilztion with potassium salts of fatty acids. Isopropanol was used as process aid compound, which also provided additional stability for producing emulsions.

For anti-bacterial effect, several emulsifiers were tested with oregano oil and sesame oil, in water.

The tested emulsifiers included: Tween 20; Tween 80; Triton X 100; Lecithin; SDS; Sodium Stearate and Potassium fatty acid. Each emulsifiers was tested at the following concentrations (in percentage) 1;5;10;15;20 for a mixture of water containing 25% oregano oil with 5% sesame oil.

The stability during the first 24 hours (i.e. lack of phase separation) and anti-bacterial activity of each emulsion were determined. Anti bacterial activity was determined by measuring the inhibition zones of 20 µl emulsion towards the following plant pathogenic bacteria: Clavi bacter; *Xanthomonas* and *Streptomyces* spp. and by spraying the emulsions on pepper plants as test plants for phytotoxicity symptoms.

The results showed that potassium fatty acid was the most suitable material in creating stable emulsion at 10% concentration; the inhibition zone of the potassium salt of fatty acid was greater than the other tested emulsions and had no phytotoxicity on pepper plants. The data obtained (not shown) clearly demonstrated phytotoxicity on pepper plants when the emulsifiers were Tween 20 Tween 80, Triton X100 or SDS, as the plants sprayed with the emulsions created therewith died, while being very vital when sprayed with the sodium stearate potassium fatty acid.

In a different set of experiments, the oregano oil and surfactant were absorbed on silica beads (with the air of isopropanol, as described above). Good anti-bacterial results were obtained when 0.5% of oregano-based powder was dispersed in water. This powder contained about 25% of oregano oil and 10% of potassium fatty acids emulsifier, namely, a concentration of 0.125% oregano oil in emulsion was active enough and needed only 0.05% of surfactant to be solubilized from the powder form.

Surprisingly, even a lower concentration of powder was sufficient to produce good crop protection in a greenhouse study. Only 0.2% of powder and consequently 0.05% of oregano oil was enough to disperse in water (to form an emulsion) and showed excellent and repeatable anti-bacterial effect with the plants being treated therewith remaining completely vital as compared to infected, but untreated control.

Preparation of Biocontrol Cocktails

Three biocontrol cocktails were prepared as follows:

The antagonistic gels containing a cocktail of the bacteria listed in Table 1 above, were each used at an amount $10^7$-$10^8$ CPU/ml from each antagonist.

Each of the antagonistic gels were then used in two concentrations, the first as obtained, i.e. with no dilution (at an amount $10^7$-$10^8$ CPU/ml from each antagonist) mixed with beads carrying 0.03% natural oil (equivalent to 1 gr beads in 1 liter water) referred to by the abbreviation NB, and a second formulation diluted ×2 with water to form formulation NBx2 in which the concentration of the oil is 0.06%.

Biocontrol Experiments

In the bio-control assays, the following oil powder composition was employed:

Materials and compositions

Oils: Sesame oil 100% (SPAline Lot sicP1A11/01); Oregano oil 100% (SPAline Lot 0015181)

Surfactant: Zohar PT-50 (Zohar Dalia, Batch 05511PM1142);

$SiO_2$ particles: Sipernet 50S (20 µm, Evonik Industries, lot 1462)

Alcohol: Isopropanol (IPA, Gadot).

Formulation:

| Amount | Oregano oil | Sesame oil | Zohar PT-50 | Sipernat 50S | IPA | Total |
|---|---|---|---|---|---|---|
| Kg | 40 | 10 | 31 | 75 | 21 | 177 |
| % | 22.6 | 5.6 | 17.5 | 42.4 | 11.9 | 100 |

Preparation of Powder

First, the oregano oil and sesame oil were mixed, to which IPA was added until a homogenous solution was obtained. To the solution, the surfactant was added by mixing until a non-viscous homogenous solution was obtained. The solution was sprayed on the $SiO_2$ powder and mixing was performed using low sheer force equipment until all liquid was absorbed and continued for an additional period of 15-30min. Then the powder was grind to breakdown aggregates and sieved through mesh 1,000 µm. For storage, the bag containing the powder was hermetically sealed and stored. Storage was for at least 2 years, at 15-30° C.

BIOCONTROL EXAMPLE 1

In vitro Effects of Biocontrol Cocktail on Various Pathogens

Tested pathogens: the following four antagonistic bacteria were tested (identified by the deposit accession number): CBS 133252, CBS 133254, CBS 134567 and CBS 133259.

*Clavibacter, Xanthomonas campestris* pv. *Vesicatoria* and Yeast—were taken from the private collection of the inventor.

Method:

Pathogen preparation—Each of the tested pathogens were separately plated on an yeast extract dextrose agar (YDC) and grown for 48 h at 25±1° C., after which the surface of each plate was washed with sterile distill water. The pathogen was then collected into tubes containing sterile distilled water. For the testing, the two tested pathogens were combined and plated on a petri dish.

Antagonist preparation—The antagonist was prepared by spreading a sample (100 μl) of one of the above listed test antagonists, on the surface of a Petri dish containing YDC media and growing the antagonist for 48 h at 25±1° C. on Antagonistic media (the agar based gel disclosed herein). Then, with a cork cutter, pieces of the media including the antagonist cocktail were removed and placed on the surface of plates carrying the two pathogens for combined incubation.

After 24 h of incubation at 25±1° C. of the pathogen together with each antagonist, an inhibition zone around the pieces of the antagonists were creating. The inhibition zones were exhibited by a halo around colonies. FIG. 5A shows the growth of pathogen bacteria without treatment with an antagonist, FIG. 5B shows the effect of CBS 133252, FIG. 5C shows the effect of CBS 133254, FIGS. 5D shows the effect of CBS 133567 and FIG. 5E shows the effect of CBS 133259

BIOCONTROL EXAMPLE 2

Effects of Biocontrol Cocktail on Tomato Wilt

In vivo evaluations were conducted in three net greenhouses to assess the antibacterial activity of the three biocontrol cocktails on tomato *Daniella* plants. The tomato plants were grown with trellises.

As the positive control, the Copper Hydroxide (Kocide, Milchan Bros) was used at a concentration of 0.3% (the Copper control)

Non-treated plants were used as Negative Control.

All plants were watered with either 50ml of a biocontrol cocktail, the Copper Control or with none (Negative Control) for three consecutive days after planting, followed by spraying the plants every 7 days. For spraying the essential oil powder (in the respective amount) and the antagonistic gel were mixed directly in the container of a backpack motor sprayer and the entire plant, including leaves and stems, were sprayed.

After 2 weeks, the second plant in each growing row in the greenhouse was infected with CBM inoculum comprising two CBM strains isolated from infected plants grown in the Besor area of Israel. The inoculum included 2 strains of CBM, strain number 32 (strain designation 189/1-1) and strain number 42 (stain designation 189/6-1) [Frida Kleitman et al. Characterization of *Clavibacter Michiganensis* Subsp. *Michiganensis* population in Israel *Eur. J. Plant Pathol* (2008) 121:463-475]

Inoculation was performed by creating a cut in a leaf of the plant, near the stem, and dipping the leaf in the CBM inoculum.

During growing, the plants were under surveillance and plants that were infected were observed.

Statistical Test

The results were analyzed using the Student's T-test.

Results

The above field trial was repeated six times, and the results of the six repetitions are summarized in Table 11A, providing mortality rate of the tomato plant, and Table 11B providing infection level by CBM, as tested using Agria kit for CBM (Cmm ImmunoStrip Test catalog no. STX 44001 Agdia Incorporated 30380 County Road 6 Eelkhart, Ind. 46514 USA)

TABLE 11A

Survival rate of tomato plants

| Treatment | Mortality Rate |
|---|---|
| Negative Control | 18% |
| Copper Control | 8% |
| NB | 2% |
| NBx2 | 1% |

TABLE 11B

Percent of CBM infection in tomato plants

| Treatment | CBM infection |
|---|---|
| Negative Control | 83.5 ± 11 |
| Copper Control | 58.8 ± 15 |
| NB | 50.5 ± 14 |
| NBx2 | 25.8 ± 12 |

Table 12 provides statistical comparison between the results of Table 11A.

TABLE 12

Statistical comparison in mortality rate between treatment groups

| Compared Groups | $P < 0.05$ |
|---|---|
| No treatment vs. NBx2 | Yes |
| No treatment vs. NB | Yes |
| No treatment vs. Copper formulation | No |
| Copper formulation vs. NB | Yes |
| NB vs. NBx2 | Yes |

In the Table "YES" indicates that there is a statistical significant difference; while "NO" indicating that there is no statistical significant difference Table 9 shows that when comparing NB to any other treatment group, the positive effect is statistically significant. When comparing Copper Control to Negative Control, the positive effect of the Copper Hydroxide treatment is insignificant. Doubling the dose (concentration of NB vs. NB×2) show also a statistically significant increased effect.

Figure 6:
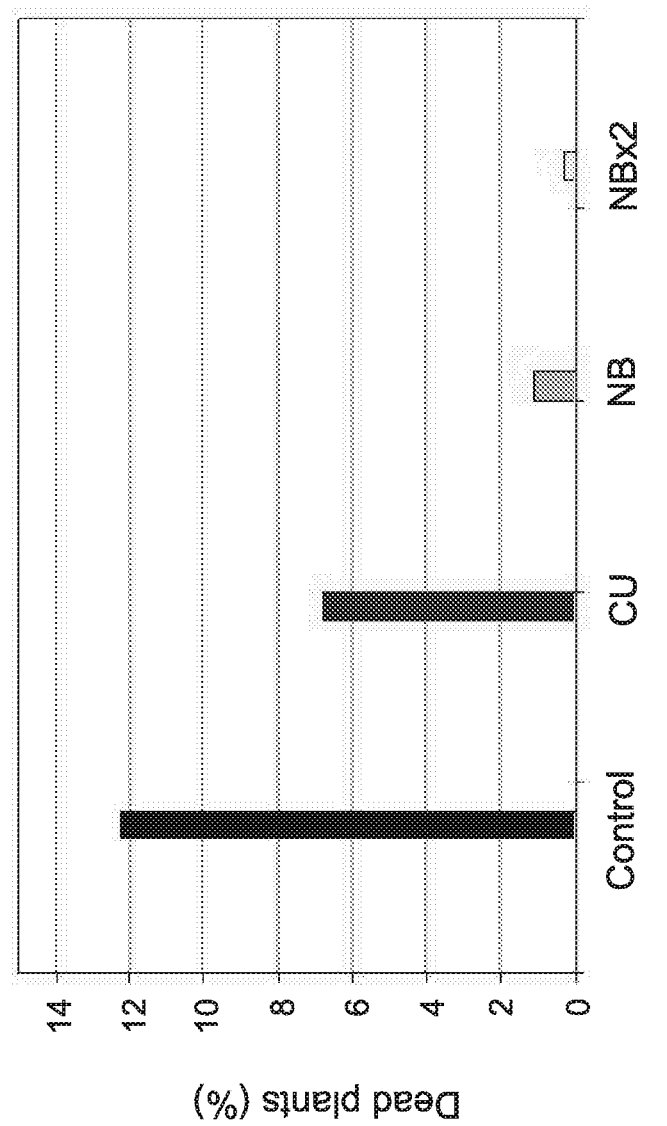
FIG. 6 is a graph showing the mortality rate of tomato plants following exposure to *Clavibacter michiganensis* subsp. *Michiganensis* (CBM), the plants were either treated with combinations according to some embodiments of the present disclosure, or with controls before inoculation with CBM.

In addition, Table 13 and FIG. 6 show the effect of treatment on plant death.

TABLE 13

| Treatment | % Mortality |
|---|---|
| | mortality |
| Negative Control | 18% |
| Copper Control | 8% |
| NB | 2% |
| NBx2 | 1% |

Specifically, Table 13 shows that non-treatment, Negative Control Group (control) and the Copper Group (Cu) have higher percentage of mortality as compared to the treatment groups NB and NBx2. In each group, the side row was more sensitive than the centered row (not shown). The difference between the side rows and centered rows may be attributed to the location of the side rows in the greenhouse, being affected by external parameters.

The results also show synergism. Table 14 shows that at a wide temperature range the combination of the natural oils (sesame oil beads and oregano oil beads) with the antagonists increase the survival of the plants to a much greater extent than the effect of each component alone [(A+B)/C>1].

Specifically, the results show that the combined effect of antagonists only (A) and oils only (B), divided by the Control (C) is greater than 1, i.e. synergism.

TABLE 14

Synergism

| Temp. °C. | ONLY Antagonist ("A") | % of the Control ("A") | Antagonist and Oils ("C") | % of the Control ("C") | Only Oils ("B") | % of Control ("B") | Untreated (Control) | % Untreated (Control) | A + B/C |
|---|---|---|---|---|---|---|---|---|---|
| 18 | 3.33* | 60 | 0 | 0 | 3.3 | 66 | 5 | 100 | Yes |
| 20 | 14.2 | 65.4 | 0 | 0 | 15.8 | 72.8 | 21.7 | 100 | Yes |
| 25 | 35.8 | 44.8 | 4.2 | 5.3 | 64.2 | 80.25 | 80 | 100 | Yes |
| 28 | 44.2 | 45 | 5 | 5.1 | 66.7 | 67.9 | 98.3 | 100 | Yes |
| 32 | 39.2 | 53.5 | 0 | 0 | 54.2 | 73.9 | 73.3 | 100 | Yes |

BIOCONTROL EXAMPLE 2

Effects of Biocontrol Cocktail on Pepper

For the prevention of pepper infection by *xanthomonas vesicatoria* (XV), the same biocontrol cocktail used in Example 1 is used, with the same treatment methodology. The pathogen was originally isolated by the inventor from diseased pepper plants and pepper seedlings. The isolates of *xanthomonas vesicatoria* (XV), are in the collection of G. Kritzman.

BIOCONTROL EXAMPLE 3

Effects of Biocontrol Cocktail on Potato

For the prevention of potato infection by *Streptomyces* spp., the causing agent of *Streptomyces scabies*., a biocontrol cocktail comprising three antagonists isolates obtained according to the procedure provided above with some of the previous list, were used. The three antagonists are provided in Table 15 below.

TABLE 15

| Deposited Antagonists for potato treatment | | |
|---|---|---|
| Antagonist | Accession No. | Name |
| *Pseudomonas mediterranea* AN1 | CBS134566 | BN13-01 |
| *Pseudomonas chlororahis* AN10 | CBS134567 | BN13-02 |
| *Pseudomonas* species AN21 | CBS134568 | BN13-03 |

The biocontrol cocktails are prepared as described above, at three concentrations 1% (no dilution); 0.5% (1:1 dilution) and 0.025% (1:4 dilution) active ingredient (of the oil formulation) with a constant concentration of the bacterial antagonists at a final concentration in the tank mix of $10^3$ CFU/ml.

Before use, the antagonists are mixed in a mixing tank with one of the dry formulations contained among others ingredient Organo oil dry powder and Sesame oil dry powder (80:20 ratio as described above). The potato seeds tubers are entered into a spraying cell by rolling on a conveyer. In the cell the tubers pass through a cloud of drops (about 80u in diameter each). After each tuber is rolled about 8 times around its axis the treated tubers are collected in a container as dry treated tubers. The treated tubers now are coated with a fine layer of the complete formulation are ready to be planted not before 72 h after the treatment.

In the case of the potato scab, the efficiency of the treatment is tested not by artificially inoculating tubers but by choosing potato seeds lots naturally high infested with many typical symptoms on each seed tuber. It could be of the common scab type or of the deep pitted scab symptoms. The seeds are examined in two procedures:

a) Samples of 60 tubers in replications are taken to the laboratory. In the laboratory all the tubers are peeled by a commercial potato peeler which is operated without watering the tubers during the peeling procedure. A large sample of the potato peels are collected. Ten grams are taken to a Stomacher bag containing 90 ml of 0.1% (w/v) water agar supplemented with 0.05% (w/v) ascorbic acid. This suspension is mixed for 2 h on a rotary shaker and then for 1 min in stomacher. After this homogenization a tenfold dilutions is done and aliquots of 100 μl were inoculated on the surface of Petri dishes containing semi selective media for isolation of Streptomyces. After 5 incubation days at 28° C. the CFU/gr peel is calculated for the treated potato seeds and in comparison with the untreated control.

b) The treated and the untreated potato seeds are planted in a trial field with at least a 4 replication each. In such experiment the growth and yield parameters as well as the scab control on the daughter tubers at the harvest time are evaluated.

The population of Streptomyces per gram of peel was calculated and the results are in Table 16:

TABLE 16 treatment of Potato scab

| Oil component dilution | *Streptomyces* spp. CFU/gr peel |
|---|---|
| No dilution (1% w/v) | 40 |
| 1:1 | $3 \times 10^2$ |
| 1:2 | $1 \times 10^4$ |
| Control (untreated) | $1 \times 10^7$ |

Further biocontrol Experiments

For testing treatment or prevention of other pathogenic infections, the following protocols may be used.

I. Protocol for In Vitro Antagonistic Activity

Transfer each antagonistic bacteria in a separate Petri Dish (9 cm) using a bacteriological transfer loop to form a single antagonist line along the diameter of the dish, and incubate the dish for 48 h at 28° C.

Transfer a tested pathogen along a line perpendicular to the antagonistic line without touching the walls of the dish.

Incubate the dishes for a further period of 5 days at a temperature between 25° C. and 28° C.

Measure the zone at which the antagonist inhibited growth of the pathogen (the "inhibitory zone"). The size of the inhibitory zone being indicative of the level of antagonistic activity of the bacteria.

II. Affect of Oil Formulation without Antagonist.

Create a stock solution of the oil formulation (described above, without the antagonistic bacteria) by dissolving the oil powder in the medium that is suitable for culturing the tested pathogen bacteria (culture medium which includes agar that is liquid at 37° C.) at a final concentration of oil of 1% w/v. From the stock solution, create a series double diluted concentrations with the culture medium (dilutions of 1:1, 1:2, 1:4, 1:16, 1:32, 1:64, 1:128, 1:256 and 1:512) of the oil formulation. Introduce into Petri dishes and allow the oil containing medium to harden.

Prepare pathogen suspension by dilution with saline colonies after 48 h of cultivation and calibrate pathogen concentration in the suspension to reach an absorbance of 0.6AU at 480 nm.

Dilute the pathogen bacteria up to a concentration of $10^{-8}$/ml and plate 100 μl on the hardened oil containing culture media.

After 5 days of incubation at 25° C-28° C. of each plate at the different oil concentrations, determine the number of colonies.

III. Bactericide or Bactriostat Activity

Prepare antagonist formulations with different amounts of oil diluted as described above, albeit with sterilized water and each diluted oil formulation with the antagonists at constant concentration of $10^3$ antagonists per ml.

An amount of 9 ml antagonists formulations with the different oil dilutions was incubated in a tube with an aliquot of 1 ml of a tested pathogen suspension in a concentration of $10^8$ CFU/ml. The pathogen suspension was prepared from cultures after 72 h cultivation.

After incubation for 3 h, the content of each tube is filtered on a 0.45 mm mesh membrane with sterilized water after which the pathogen is washed off from the membrane using sterilized water and vortexing.

The washed off bacteria are then tenfold diluted in a series up to a concentration of $10^{-8}$ CFU/ml. From each dilution 100 μl aliquots are platted on a Petri dish with a suitable culture media and cultured. The formation of colonies is indicative of bacteriostat activity of the formulations while absence of colonies is indicative of bacteriocidal activity.

IV. Plant Testing:

The plant testing is conducted in a pot or in a green-house. Plants with at least 5 leaves are used for testing.

In a pot:

On day 1, the plant is sprayed with the tested oil/antagonist formulation at various concentrations and after 12 h the plant is sprayed with the pathogen solution being at a concentration of about $10^6$ CFU/ml.

Two hours after infection, the plants are once again sprayed with the same oil/antagonist formulation again and is continuously sprayed every 6 days for a period of 6 weeks. After 6 weeks, the disease incidence is estimated and recorded.

In an Open Test Field or Greenhouse:

The plants are grown using the conventional method of their planting and growing in the field of greenhouse.

After planting, the plants are irrigated with an amount of about 100ml oil/antagonist formulation /plant and then each plant is sprayed with the same formulation, with continuous spraying every 5 -6 days.

The disease incidence is estimated and recorded.

Toxicology Tests

Various toxicological tests were performed using the formulation including a cocktail of all deposited antagonists (Table 1) each at a concentration of $10^9$ as follows:

(i) Acute Oral Toxicity in the Rat:

Protocol:

Female Sprague-Dawley™ (SD™) rats were divided into two groups (n=3), each receiving a single dose of 2000 mg/kg of the tested formulation (Dosage Volume of 1.97 ml/kg, oral gavage (PO) administration), at an interval of administration between the two groups of 24 hours.

Results:

No mortality occurred in any of the tested rats throughout the 14 days observation period.

No noticeable clinical signs in reaction to dosing were evident in any of the animals during the immediate post-dosing time or throughout the entire 14-day observation period.

Body weight gain at the end of the 14-day study period of all animals was found to be within range of normally expected values.

No gross pathological findings were evident in any of the animals at the time of their scheduled necropsy.

Based on the lack of adverse reactions following a single oral administration to the rats at the limit test dose level of 2000 mg/kg, the tested formulation may be regarded as not representing an acute toxic risk by this route of administration and the acute oral median Lethal Dose (LD50) is greater than 2000 mg/kg.

(ii) Acute Dermal Toxicity

Protocol:

A single dose level of 2000 mg/kg of the tested formulation was topically applied for 24-hr exposure duration to a 5 female and 5 male Sprague-Dawley (SD™) rats. The rats were observed for a total of 14 days.

Results:

No mortality occurred in any of the rats throughout the entire 14-day study period.

No noticeable clinical signs in reaction to dosing were evident in any of the rats throughout the entire 14-day observation period.

Body weight gain of all rats at the end of the 14-day study period was found to be within the range of normally expected values.

No gross pathological findings were evident in any of the rats at the time of their scheduled necropsy Based on the lack of adverse reactions following a single dermal application to the rats the tested formulation was as not representing an acute toxic risk by this route of administration and the estimated acute dermal median lethal dose (LD50) was determined to be greater than 2000 mg/kg.

Acute Dermal Irritation/Corrosion in Rabbits

Protocol:

The potential skin irritation effects of the tested formulation were assessed following a single dermal application to a group of 3 male NZW rabbits, according to the testing procedure recommended by the OECD Guideline for the Testing of Chemicals, Section 4, No. 404, "Acute Dermal Irritation/Corrosion" adopted 24 Apr. 2002.

Specifically, all rabbits were topically applied with a single sample of absorbent gauze measured 2×3 cm each moistened with 0.5 ml of the tested formulation for a 4 hour exposure duration. Each gauze patch was held in contact with the skin with non-irritant irritant tape and a suitable semi-occlusive dressing (TUBIGRIP stockinet) to retain the gauze patches and the tested formulation throughout the exposure period.

Dermal reactions were scored and recorded at the standard time points of 1, 24, 48 and 72 hours after patch removal.

Results:

No erythema or edema was noted throughout the 72-hour study period in any of the rabbits.

No other dermal reactions were noted in any of the rabbits throughout the study period.

No noticeable clinical signs in reaction to treatment were evident in any of the rabbits throughout the entire study period.

No abnormal changes in body weight were noted in any of the rabbits throughout the entire study period.

Consideration of the calculated Primary Irritation Index (PII) was 0, led to the conclusion that irritation response is categorized as negligible.

(iii) Skin Sensitization (Local Lymph Node Assay)

Protocol:

The potential of the tested formulation to cause skin sensitization was assessed on the basis of the testing procedures by the OECD Guideline for the Testing of Chemicals, Section 4, No. 429 "Skin Sensitization: Local Lymph Node Assay", adopted 22 Jul. 2010.

Specifically, three dilutions of the tested formulation were prepared in Physiological Saline. Pluronic® L92 (1% v/v) was added to each dosing solutions prior to application.

In order to ensure reproducibility and sensitivity of the test procedure, a well-known weak to moderate contact allergen, 25% HCA, was included in this study, diluted with the Negative Control used.

Three groups of BALB/c female mice (n=5) were subjected to application of the tested formulation (one dilution per group) once daily for three consecutive days, at a dose volume of 25 µl applied on the dorsum of each outer ear. Additional two equally sized groups were subjected to application of either the Negative Control (Physiological Saline) or the Positive Control (25% HCA), under identical conditions.

Five days after the first topical application, all mice were injected with 3H-Methyl Thymidine by intravenous (IV) injection. Approximately 5 hours later, all mice were euthanized and the auricular lymph nodes were excised. A single cell suspension of both left and right lymph nodes cells from individual animals was prepared.

The incorporation of 3H-Methyl Thymidine was measured by a β-Counter and expressed as Disintegration Per Minute (DPM)/animal.

The Stimulation Index (SI) was calculated for the groups treated with the tested formulation dilutions and the Positive Control. The SI values for all dilutions were lower than 3 and the SI values for the Positive Control was higher than 3.

Results:

No mortality occurred in any of the mice in all groups throughout the 5-day study period.

No noticeable clinical signs in reaction to treatment were observed in any of the tested formulation or Negative Control treated mice throughout the 5-day study period. All Positive Control treated mice displayed redness at the ears.

All mice showed an increase in body weights at the end of the 5-day study period.

Under the conditions of the study and according to the calculated Stimulation Index values, it was concluded that the tested formulation did not cause reactions associated with skin sensitization.

(iv) Acute Eye Irritation/Corrosion in Rabbits

Protocol:

The potential eye irritation/corrosion effects of the tested formulation were assessed following a single eye instillation to a group of 3 male NZW rabbits, according to the testing procedure recommended by the OECD Guideline for the Testing of Chemicals, Section 4, No. 405, "Acute Eye Irritation/Corrosion" adopted Oct. 2, 2012.

Initially, single dose of 0.1 ml the tested formulation was applied to the right eye of one rabbit (Initial Test) and subsequently to two additional rabbits (Confirmatory Test). The left eye of each rabbit was not treated and served as control.

Ocular reactions were scored and recorded at the standard time points of 1, 24, 48 and 72 hours following application.

Results:

No ocular reaction was noted throughout the 72-hour study period in any of the rabbits.

No noticeable clinical signs in reaction to treatment were evident in any of the rabbits throughout the entire study period.

No abnormal changes in body weight were noted in any of the rabbits throughout the entire study period.

Under the conditions of this study, it was concluded that the tested formulation did not cause reactions associated with eye irritation/ corrosion.

The invention claimed is:

1. A package comprising:
   i) at least one first component comprising particulate matter comprising at least one natural oil and at least one surfactant; and
   ii) at least one second component comprising at least one antagonist of a microbial pathogen, wherein the at least one antagonist is at least one bacteria selected from the group consisting of *Pseudomonas* species (Accession No. CBS133252), *Pseudomonas alcaliphila* (Accession No. CBS133254), *Bacillus subtilis* (Accession No. CBS133255), *Pseudomonas cedrina* (Accession No. CBS133256), *Pseudomonas* species (Accession No. CBS133257), *Pseudomonas* species (Accession No. CBS133258), *Pseudomonas* species (Accession No. CBS134568), *Achromobacter spanius* (Accession No. CBS133259), *Pseudomonas mediterranea* (Accession No. CBS134566), and *Pseudomonas chlororahis* (Accession No. CBS134567), and wherein the at least one first component and the at least one second component are contained in separate compartments of said package.

2. The package of claim 1, wherein said first component comprises the particulate matter in an essentially dry form.

3. The package of claim 1, wherein:
(a) said particulate matter comprises silica ($SiO_2$); or
(b) said particulate matter has a size distribution in the range of 10-25 μm; or
(c) said particulate matter exhibits at least one of a surface area in the range of 400-500 $m^2$ $N_2$/g and oil capacity in the range of 300-350 DBP/100 gram particulate; or
(d) said natural oil is absorbed in said particulate matter; or any combinations of (a)-(d).

4. The package of claim 1, wherein said at least one natural oil comprises at least one essential oil.

5. The package of claim 1, wherein the particulate matter of the first component comprises:
(i) at least one population of particulate matter comprising a mixture of at least two natural oils, wherein the at least two natural oils comprise at least one essential oil and at least one carbon-rich nutrient oil; or
(ii) two or more populations of particulate matter, wherein each population of particulate matter comprises a different type of natural oil,
wherein at least one population of particulate matter comprises an essential oil, and at least one population of particular matter comprises carbon-rich nutrient oil; or
(iii) a combination of (i) and (ii).

6. The package of claim 1, wherein the particulate matter comprises between 20% to 50% w/w natural oil out of the total weight of the particulate matter.

7. The package of claim 1, wherein said second component is in a form of a gel.

8. The package of claim 1, wherein said at least one antagonist is a soil born bacteria or a bacteria isolated from a plant part, wherein the plant exhibits tolerance or resistance to the microbial pathogen.

9. The package of claim 1, wherein the at least one second component comprises an antagonist at a concentration of between 500 CFU/ml to 5,000 CFU/ml.

10. The package of claim 1, further comprising two or more second components, wherein each of said second components carry a different type of the antagonist or a cocktail of the antagonists.

11. The package of claim 1, further comprising:
one or more first wells holding said at least one first component;
one or more second wells holding said at least one second component;
wherein the one or more first wells and the one or more second wells each have a top opening and a recess extending downwardly from said top opening, and the wells are held together in an essentially planar matrix; and
a first film sealing the openings of the one or more first wells and a second film sealing the openings of the one or more second wells.

12. The package of claim 11, wherein at least one of said one or more first wells and one or more second wells are either (i) integrally formed in said planar matrix or (ii) reversibly mountable in an opening or recess within said planar matrix.

13. The package of claim 11, wherein said first film is an oil compatible and fluid impermeable thermoplastic polymeric film.

14. The package of claim 11, comprising a single first well and a plurality of second wells, each second well comprises the same or different antagonist or a cocktail of antagonists.

15. The package of claim 11, comprising a single second film sealing said one or more second wells, wherein the second film is permeable to gas; said second film is superimposed over said first film and optionally fixedly attached to said first film.

16. The package of claim 1, wherein the at least one antagonist of the at least one second component is a mixture of the antagonists.

\* \* \* \* \*